United States Patent
Wang et al.

(10) Patent No.: US 9,409,857 B2
(45) Date of Patent: Aug. 9, 2016

(54) AGOMELATINE SULFURIC ACID COMPLEX, AND PREPARATION METHOD AND APPLICATION THEREOF

(71) Applicant: SHANGHAI RIGHTHAND PHARMTECH. CO., LTD., Shanghai (CN)

(72) Inventors: Haiping Wang, Shanghai (CN); Cheng Chi, Shanghai (CN); Zhengming Chi, Shanghai (CN); Jin Wang, Shanghai (CN); Guanyu Xu, Shanghai (CN)

(73) Assignee: SHANGHAI RIGHTHAND PHARMTECH, CO., LTD., Shanghai (CN)

( * ) Notice: Subject to any disclaimer, the term of this patent is extended or adjusted under 35 U.S.C. 154(b) by 0 days.

(21) Appl. No.: 14/401,419

(22) PCT Filed: May 14, 2013

(86) PCT No.: PCT/CN2013/075574
§ 371 (c)(1),
(2) Date: Nov. 14, 2014

(87) PCT Pub. No.: WO2013/170738
PCT Pub. Date: Nov. 21, 2013

(65) Prior Publication Data
US 2015/0141519 A1    May 21, 2015

(30) Foreign Application Priority Data

May 14, 2012  (CN) .......................... 2012 1 0147904
Jun. 3, 2012  (CN) .......................... 2012 1 0178635
Jun. 7, 2012  (CN) .......................... 2012 1 0184481

(51) Int. Cl.
*C07C 303/02* (2006.01)
*C07C 309/04* (2006.01)
(Continued)

(52) U.S. Cl.
CPC ............ *C07C 233/18* (2013.01); *C07C 303/02* (2013.01); *C07C 309/04* (2013.01); *C07C 309/29* (2013.01); *C07C 309/30* (2013.01); *C07B 2200/13* (2013.01)

(58) Field of Classification Search
CPC ............... A61K 31/165; A61K 31/185; C07B 2200/13; C07C 233/18; C07C 303/02; C07C 309/04; C07C 309/29; C07C 309/30
USPC ...................... 514/630; 562/115, 30; 564/219
See application file for complete search history.

(56) References Cited

U.S. PATENT DOCUMENTS

2011/0313198 A1* 12/2011 Zhang ................... C07C 233/18
564/219

FOREIGN PATENT DOCUMENTS

CN       101481321       7/2009
CN       102702008       10/2012

(Continued)

OTHER PUBLICATIONS

CN 102911075 machine generated English language translation, p. 1-18, obtained Nov. 28, 2015.*

(Continued)

*Primary Examiner* — Jafar Parsa
*Assistant Examiner* — Amy C Bonaparte
(74) *Attorney, Agent, or Firm* — Joseph Meara; Foley & Lardner LLP

(57) ABSTRACT

The present invention relates to an Agomelatine sulfuric acid complex in formula (I) and the preparation method thereof ($HX=H_2SO_4$, $RSO_3H$ ($R=CH_3$, Ph, 4-$CH_3$Ph)). The solubility of the Agomelatine sulfuric acid complex obtained by the method of the present invention is significantly improved compared with Agomelatine, has good stability and higher purity, and is suitable for application in finished-product medicinal preparations. The preparation process is quite simple, and a product with high purity can be obtained without special operations.

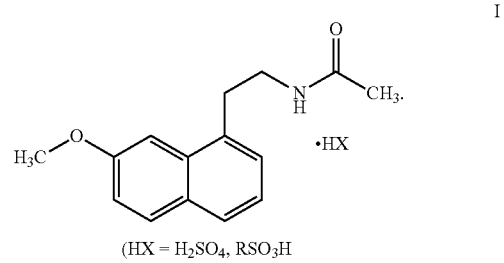

($HX = H_2SO_4$, $RSO_3H$)
($R = CH_3$, Ph or 4-$CH_3$Ph))

17 Claims, 15 Drawing Sheets

(51) Int. Cl.
 *C07C 233/18* (2006.01)
 *C07C 309/29* (2006.01)
 *C07C 309/30* (2006.01)

(56) References Cited

FOREIGN PATENT DOCUMENTS

| CN | 102702041 | | 10/2012 |
| CN | 102718675 | | 10/2012 |
| CN | 102718676 | * | 10/2012 |
| CN | 102911075 | * | 2/2013 |
| WO | WO 2012146371 | | 11/2012 |

OTHER PUBLICATIONS

CN 102718676 machine generated English language translation, p. 1-9, obtained Nov. 28, 2015.*
International Search Report for International Application No. PCT/CN2013/075574 mailed Aug. 22, 2013 (including English translation).
Written Opinion for International Application No. PCT/CN2013/075574 mailed Aug. 22, 2013 (including English translation).

* cited by examiner

| # | 2-Theta | d(Å) | I% | # | 2-Theta | d(Å) | I% |
|---|---|---|---|---|---|---|---|
| 1 | 5.759 | 15.3325 | 2.9 | 21 | 25.081 | 3.5475 | 6.4 |
| 2 | 6.100 | 14.4769 | 8.7 | 22 | 26.002 | 3.4240 | 4.5 |
| 3 | 11.342 | 7.7954 | 12.4 | 23 | 26.700 | 3.3360 | 11.5 |
| 4 | 12.202 | 7.2477 | 11.1 | 24 | 27.262 | 3.2685 | 1.0 |
| 5 | 12.520 | 7.0644 | 4.8 | 25 | 28.098 | 3.1731 | 2.7 |
| 6 | 13.781 | 6.4207 | 11.9 | 26 | 28.861 | 3.0910 | 8.5 |
| 7 | 14.278 | 6.1983 | 31.1 | 27 | 29.621 | 3.0134 | 3.8 |
| 8 | 15.339 | 5.7718 | 7.7 | 28 | 29.940 | 2.9820 | 6.1 |
| 9 | 16.399 | 5.4009 | 8.1 | 29 | 30.858 | 2.8953 | 23.7 |
| 10 | 17.619 | 5.0297 | 16.4 | 30 | 31.640 | 2.8255 | 10.8 |
| 11 | 18.421 | 4.8125 | 47.3 | 31 | 32.600 | 2.7445 | 5.1 |
| 12 | 18.820 | 4.7111 | 100.0 | 32 | 33.360 | 2.6837 | 2.0 |
| 13 | 20.900 | 4.2468 | 15.6 | 33 | 34.501 | 2.5975 | 3.5 |
| 14 | 21.080 | 4.2109 | 19.1 | 34 | 35.420 | 2.5321 | 3.9 |
| 15 | 21.440 | 4.1411 | 62.2 | 35 | 38.260 | 2.3505 | 2.9 |
| 16 | 21.943 | 4.0473 | 11.9 | 36 | 39.661 | 2.2706 | 6.1 |
| 17 | 22.801 | 3.8969 | 20.0 | 37 | 41.781 | 2.1602 | 2.6 |
| 18 | 23.820 | 3.7324 | 19.8 | 38 | 42.381 | 2.0841 | 2.5 |
| 19 | 24.139 | 3.6839 | 5.0 | 39 | 46.099 | 1.9674 | 2.3 |
| 20 | 24.560 | 3.6216 | 84.5 | | | | |

AGOMELATINE SULFURIC ACID COMPLEX, AND PREPARATION METHOD AND APPLICATION THEREOF

RELATED APPLICATIONS

This application is the U.S. National Stage of PCT/CN2013/075574, with international filing date of May 14, 2013 and which claims the benefit of and priority to CN 201210147904.8, filed May 14, 2012, CN 201210178635.1, filed Jun. 3, 2012 and CN 201210184481.7, filed Jun. 7, 2012, the contents of which are incorporated herein by reference in their entireties.

TECHNICAL FIELD

The present invention relates to a group of Agomelatine sulfuric acid complex, and preparation method and application thereof, as well as a pharmaceutical composition comprising the Agomelatine sulfuric acid complex.

TECHNICAL BACKGROUND

Agomelatine ($C_{15}H_{17}NO_2$, mw 243.31, CAS No. [138112-76-2]) also names as N-[2-(7-methoxyl-1-naphthyl)ethyl]acetamide, having the following formula.

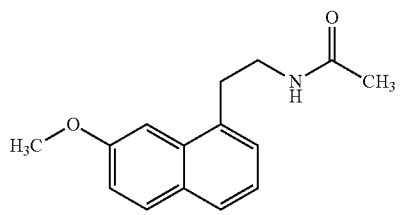

Agomelatine is a amelatonergic antidepressant, which also can antagonize 5HT2C receptor. Agomelatine was developed by the pharmaceutical company Servier (France). It is marketed for the treatment of major depressive disorder in Valdoxan as trade name, and has been reported not to produce sexual side effects. Agomelatine may also have positive effects on sleep and less adverse effects.

The description of preparation method, crystallographic form and use in the treatment of Agomelatine can be found in applications such as EP0447285, EP15694202, CN200510071611.6, CN200610108396.7, CN200610108394.8, CN200610108395.2 and CN200910047399.2. However, as to the reports about Agomelatine-related acid radical complex, only CN201010126254.x discloses hydrogen chloride hydrate of Agomelatine and preparation method thereof; CN201010126263.9 discloses hydrogen bromide hydrate of Agomelatine and the preparation method thereof; CN201010187158.6 discloses the acetic acid solvate of Agomelatine. No other acid radical complexes were disclosed in the art.

In consideration of the pharmacy value of Agomelatine, it is crucial to obtain a stable Agomelatine complex with high purity, defined crystallographic form, excellent reproductivity, and better solubility, which is suitable for producing finished pharmaceutical preparation.

SUMMARY

The present invention provides an stable acid radical complex of Agomelatine which is provided with high purity, defined crystallographic form and good reproductivity in preparation process, as well as improved solubility compared with Agomelatine, which is more advantageous for production of pharmaceutic formulation containing Agomelatine.

In order to obtain new acid radical complexes of Agomelatine, the Inventors carried out a lot of experiments and found that the Agomelatine compound can react with specific acids containing sulfur, oxygen (HX=$H_2SO_4$, $RSO_3H$ (R=$CH_3$, Ph, 4-$CH_3$Ph)), forming stable complex via hydrogen bond, wherein the sulfuric acid-, methanesulfonic acid- and benzenesulfonic acid-complex of Agomelatine provide the most preferable crystallographic forms and superior reproductivity in preparation. The complexes of the present invention show physicochemical properties meeting the requirements for medicament preparation.

Provided herein is a group of Agomelatine sulfuric acid complex having the following formula (I):

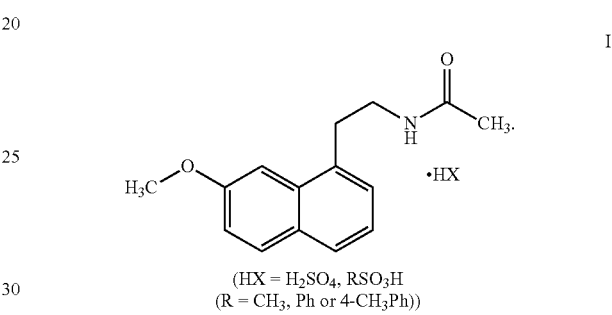

Another object of the present invention is to provide a preparation method of the Agomelatine sulfuric acid complex described above, which is formed by reaction between Agomelatine and said HX acid. The method comprises the steps of: dissolving Agomelatine in an organic solvent before adding the corresponding HX acid, crystallizing or precipitating out the product after reaction, and washing and drying the crystallization or precipitation product; or alternatively, dissolving Agomelatine in an organic solvent before adding the corresponding HX acid therein, then adding another poor solvent, crystallizing or precipitating out the product after reaction, and washing and drying the crystallization product.

Alternatively, the process can be carried out by adding Agomelatine into an organic solvent containing said HX acid, crystallizating or precipitating out the product after reaction, and washing and drying the crystallization product.

The reaction temperature for the preparation method herein can be a common temperature used in reaction in the art, with the proviso that the temperature is lower than the boiling point of the organic solvent used in the preparation process. However, in order to obtain a better crystal and improve the yield of the reaction, a reactive temperature at or below the room temperature is used, preferably below the room temperature, and more preferably in the range between 0° C. and 25° C.

For the preparation method of the Agomelatine sulfuric acid complex described above, the organic solvent is capable of dissolving the reaction materials, Agomelatine and said HX acid, as well as separating out the Agomelatine sulfuric acid complex. In these regards, the organic solvent is selected from dichloromethane, chloroform, acetone, C1-C4 alcohol, methyl acetate, ethyl acetate, tetrahydrofuran, acetonitrile and the like which are commonly used, preferably dichloromethane and acetone for HX=$H_2SO_4$, dichloromethane, acetone and C1-C4 alcohol for HX=$RSO_3H$ (R=Ph, 4-CH$_3$Ph), and ethyl acetate, and isopropyl acetate for HX=CH$_3$SO$_3$H. As used in the above preparation method, "poor solvent" refers to a solvent in which the product Agomelatine sulfuric acid complex presents a poor solubility. A useful "poor solvent" can be methyl acetate, ethyl acetate, isopropyl acetate, acetone, methyl isobutyl ketone and the like, preferably ethyl acetate, isopropyl acetate and acetone for HX=H$_2$SO$_4$, or RSO$_3$H (R=Ph, 4-CH$_3$Ph), and ethyl acetate and isopropyl acetate for if HX=CH$_3$SO$_3$H.

The Agomelatine sulfuric acid complex presents as a crystal, wherein HX=H$_2$SO$_4$, or RSO$_3$H (R=CH$_3$, Ph). The crystallographic forms thereof were determined via X-ray powder diffraction, and characterized with Bragg 2-Theta (Bragg 2θ), interplanar spacing (d), and relative intensity (I) as follows (FIGS. 1, 7, 11 and 14):

| HX = H$_2$SO$_4$ (Agomelatine sulfuric acid complex) | | |
|---|---|---|
| 2-Theta | d(Å) | Relative Intensity (I %) |
| 6.959 | 12.6922 | 13.7 |
| 11.621 | 7.6087 | 64.8 |
| 14.139 | 6.2587 | 18.1 |
| 16.979 | 5.2177 | 22.3 |
| 17.640 | 5.0236 | 56.7 |
| 18.660 | 4.7512 | 90.6 |
| 19.818 | 4.4762 | 17.1 |
| 20.541 | 4.3202 | 56.6 |
| 21.659 | 4.0996 | 19.9 |
| 23.420 | 3.7953 | 76.5 |
| 23.961 | 3.7107 | 22.9 |
| 24.461 | 3.6361 | 88.0 |
| 24.841 | 3.5813 | 100.0 |
| 25.799 | 3.4505 | 15.8 |
| 27.040 | 3.2949 | 19.7 |
| 27.881 | 3.1973 | 26.3 |
| 30.220 | 2.9550 | 17.9 |
| 30.781 | 2.9024 | 16.9 |

| HX = CH$_3$SO$_3$H (Agomelatine methanesulfonic acid complex) crystallographic form A | | |
|---|---|---|
| 2-Theta | d(Å) | Relative Intensity (I %) |
| 7.241 | 12.1977 | 10.5 |
| 9.301 | 9.5005 | 5.6 |
| 11.680 | 7.5704 | 15.5 |
| 12.879 | 6.8680 | 4.9 |
| 14.258 | 6.2068 | 7.4 |
| 15.641 | 5.6609 | 100.0 |
| 17.498 | 5.0640 | 59.0 |
| 18.660 | 4.7512 | 10.1 |
| 20.217 | 4.3886 | 21.5 |
| 21.041 | 4.2187 | 11.0 |
| 22.038 | 4.0300 | 39.7 |
| 22.801 | 3.8969 | 53.5 |
| 24.839 | 3.5815 | 19.9 |
| 26.199 | 3.3987 | 31.4 |
| 26.841 | 3.3188 | 5.5 |
| 27.841 | 3.2018 | 32.2 |
| 31.581 | 2.8306 | 13.5 |
| 32.142 | 2.7825 | 10.9 |

| HX = CH$_3$SO$_3$H (Agomelatine methanesulfonic acid complex) crystallographic form B | | |
|---|---|---|
| 2-Theta | d(Å) | Relative Intensity (I %) |
| 7.679 | 11.5031 | 9.7 |
| 14.302 | 6.1878 | 2.8 |
| 15.420 | 5.7415 | 100.0 |
| 16.221 | 5.4596 | 3.3 |
| 18.416 | 4.8138 | 2.4 |
| 19.060 | 4.6524 | 4.9 |
| 20.040 | 4.4271 | 10.5 |
| 20.600 | 4.3081 | 21.0 |
| 21.221 | 4.1834 | 6.1 |
| 22.060 | 4.0261 | 12.2 |
| 22.439 | 3.9589 | 10.9 |
| 23.080 | 3.8504 | 8.7 |
| 25.861 | 3.4423 | 4.6 |
| 26.380 | 3.3757 | 10.3 |
| 26.960 | 3.3044 | 5.7 |
| 33.299 | 2.6884 | 4.3 |

| HX = PhSO$_3$H (Agomelatine benzenesulfonic acid complex) | | |
|---|---|---|
| 2-Theta | d(Å) | Relative Intensity (I %) |
| 6.100 | 14.4769 | 8.7 |
| 11.342 | 7.7954 | 12.4 |
| 12.202 | 7.2477 | 11.1 |
| 13.781 | 6.4207 | 11.9 |
| 14.278 | 6.1983 | 31.1 |
| 17.619 | 5.0297 | 16.4 |
| 18.421 | 4.8125 | 47.3 |
| 18.820 | 4.7111 | 100.0 |
| 20.900 | 4.2468 | 15.6 |
| 21.080 | 4.2109 | 19.1 |
| 21.440 | 4.1411 | 62.2 |
| 21.943 | 4.0473 | 11.9 |
| 22.801 | 3.8969 | 20.0 |
| 23.820 | 3.7324 | 19.8 |
| 24.560 | 3.6216 | 84.5 |
| 26.700 | 3.3360 | 11.5 |
| 30.858 | 2.8953 | 23.7 |
| 31.640 | 2.8255 | 10.8 |

The above results also cover the crystals of which the diffraction peaks are within the error limits of ±0.2°.

Additionally, HX=4-CH$_3$PhSO$_3$H (Agomelatine p-toluenesulfonic acid complex) is an amorphous solid.

For the crystallographic form of the Agomelatine benzenesulfonic acid complex described above (HX=PhSO$_3$H), it is shown that the single crystal X-diffraction thereof belongs to an orthorhombic crystal system, with a space group of P2$_1$2$_1$2$_1$, cell parameters: a=8.0780(5)Å, b=8.5765(6)Å, c=28.920(2)Å, α=β=γ=90.0°, cell volume V=2003.6(2)Å$^3$, and the number of asymmetric units in the cell Z=4 (FIGS. 15 and 16). The molecular space structure shows that there are hydrogen bonds between the NH in the Agomelatine molecule and the O in the benzenesulfonic acid molecule, as well as the OH in the benzenesulfonic acid molecule and the O in the Agomelatine molecule, suggesting the absolute molecular conformation of the Agomelatine benzenesulfonic acid complex.

Analysis measures such as nuclear magnetic resonance (NMR), mass spectrum (MS), infrared spectroscopy, TGS, DSC and the like were further carried out to characterize the Agomelatine sulfuric acid complex described above.

For the NMR results of the Agomelatine sulfuric acid complex, the H NMR spectroscopy in d$_6$-DMSO clearly shows two active hydrogens of the sulfuric acid and one active hydrogen in the amide group within the Agomelatine molecule (see FIG. 5), indicating that there is one molecule of sulfuric acid contained in the Agomelatine sulfuric acid complex, and these three active hydrogens atoms are stabilized due to the presence of the hydrogen bonds between the molecules, which demonstrates that the Agomelatine molecule and sulfuric acid molecule form a complex rather than a simple mixture. H NMR spectroscopy was determined upon adding small amount of $D_2O$ into $d_6$-DMSO, and the spectrum shows that all three active hydrogen atoms have been exchanged (see FIG. 6), which further confirms the presence of the $HX=H_2SO_4$ structure in formula (I).

The Agomelatine sulfuric acid complex described above, i.e. the structural composing of formula (I) ($HX=H_2SO_4$), was further confirmed through the following three measures:

1) Elemental analysis: elemental analysis for the sulfur element (S) in the Agomelatine sulfuric acid complex was performed. The measured S % is 9.23%, which is close to the theoretical S value 9.39% of formula (I) ($HX=H_2SO_4$).

2) HPLC external standard content analysis: the Agomelatine content in the Agomelatine sulfuric acid complex was determined with Agomelatine standard as a reference. The measured Agomelatine content in the complex is 71.48%, which is close to the theoretical value 71.27% in formula (I) ($HX=H_2SO_4$).

(3) barium sulfate gravimetric analysis: a predetermined amount of Agomelatine sulfuric acid complex was dissolved into methanol and hydrochloric acid, and the sulfate radicals were completely precipitated with barium chloride; through determining the weight of barium sulfate, the sulfate radicals converted to constitute 28.63% of the above complex, which is close to the theoretical sulfate radical content of 28.14% within formula (I) ($HX=H_2SO_4$).

For the NMR results of the Agomelatine methanesulfonic acid complex crystal described above, the H NMR spectroscopy in $CDCl_3$ shows the active hydrogen of methanesulfonic acid and the active hydrogen of amide group in the Agomelatine molecule, and the methyl peak of methylsulfonic acid (FIG. 12), suggesting that there is one molecule of methanesulfonic acid contained in the Agomelatine methanesulfonic acid complex, and the active hydrogen atom are stabilized due to the presence of the hydrogen bonds between the molecules. According to the MS analysis, $ESI^+$ shows a quasimolecular ion peak m/z of 244.1 $[M+H]^+$, which is consistent with the molecular weight of Agomelatine, 243.3. $ESI^-$ shows a quasimolecular ion peak m/z of 94.93 $[M-H]^+$, which is consistent with the molecular weight of methylsulfonic acid, 96.11 (FIG. 13). The above results demonstrate that the Agomelatine and the methanesulfonic acid form a complex rather than a simple mixture.

The pharmacological study of the Agomelatine acid radical ($HX=H_2SO_4$, $RSO_3H$ ($R=CH_3$, Ph, 4-$CH_3Ph$)) complex provided herein shows that the complex can be used for treating diseases such as melatoninergic system diseases, sleep disturbance, nervous, anxiety, seasonal affective disorder or major depressive disorder, cardiovascular diseases, digestive system diseases, fatigue, schizophrenia, Panic disorder, depression and the like.

The Agomelatine acid radical ($HX=H_2SO_4$, $RSO_3H$ ($R=CH_3$, Ph, 4-$CH_3Ph$)) complex provided herein can be made into various dosage forms with various pharmaceutically acceptable excipient, for orally or injection application; an effective dose can be properly adjusted according to the severity of the disease to be treated, the administration route, and the age and weight of the patient; the daily dose can be in the range between 0.1 mg and 1 g, administered either in a single dose or at any interval.

The term "pharmaceutically acceptable excipient(s)" as used herein refers to the supplementary material used for administering therapeutic agent(s), including various excipients and diluents. The term refers to supplementary materials for medicaments that they are not the essential active constituents themselves and provide no toxicity upon application. Suitable supplementary materials are well known to those ordinarily skilled in the art. A full discussion of the pharmaceutically acceptable excipient can be found in Remington's Pharmaceutical Sciences (Mack Pub. Co., N.J. 1991). The pharmaceutically acceptable excipient useful in a composition can include liquids, such as water, brine, glycerin and ethanol. Additionally, further auxiliary substances may exist in these supplementary materials, such as disintegrants, moistering agents, emulsifying agents, pH-buffering agents and the like.

BRIEF DESCRIPTION OF THE DRAWINGS

Detailed descriptions are provided to the preferred examples of the present invention with reference to the following drawings for better understanding of the objects, characteristics and advantages of the present invention, wherein.

DETAILED DESCRIPTION

Further explanation or description of the contents of the present invention is provided with the following examples. The provided examples are not intended to limit the protection scope of the present invention.

EXAMPLE 1

10.0 g of Agomelatine was dissolved into 50 mL of dichloromethane under stirring; 4.1 g of concentrated sulfuric acid was added at 10° C., allowing solid to be separated out under stirring, and the stirring was continued and the reaction was cooled to 0° C. for complete solid separation; the reaction was filtrated and the solid was washed twice with 10 mL of dichloromethane, dried at 80° C. to obtain 13.4 g of product as a white solid; purity: 99.5%, yield rate: 95.5%. mp: 154.0-158.0° C. KF: 0.465%.

EXAMPLE 2

Figure 1:
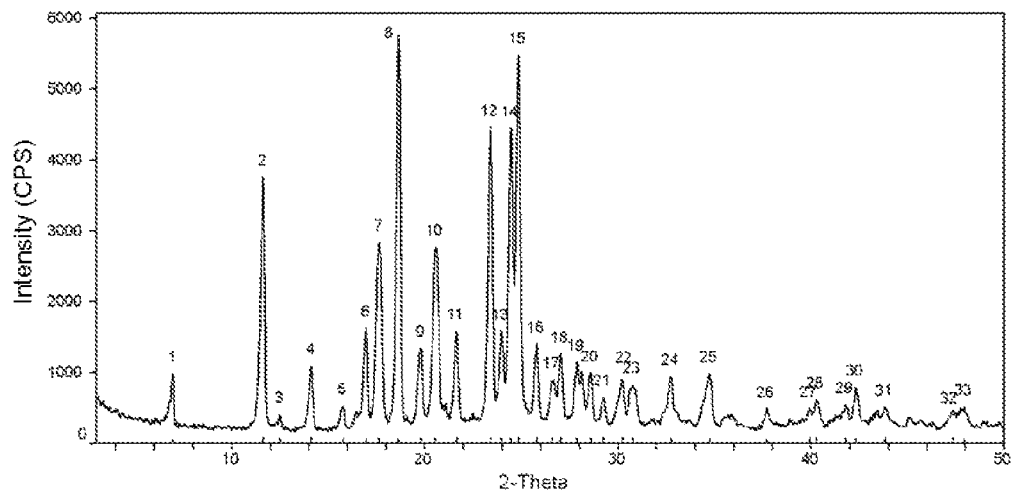
FIG. 1 is the powder X-Ray Diffraction (XRD) spectrum of the crystal Agomelatine sulfuric acid complex.
Figure 2:
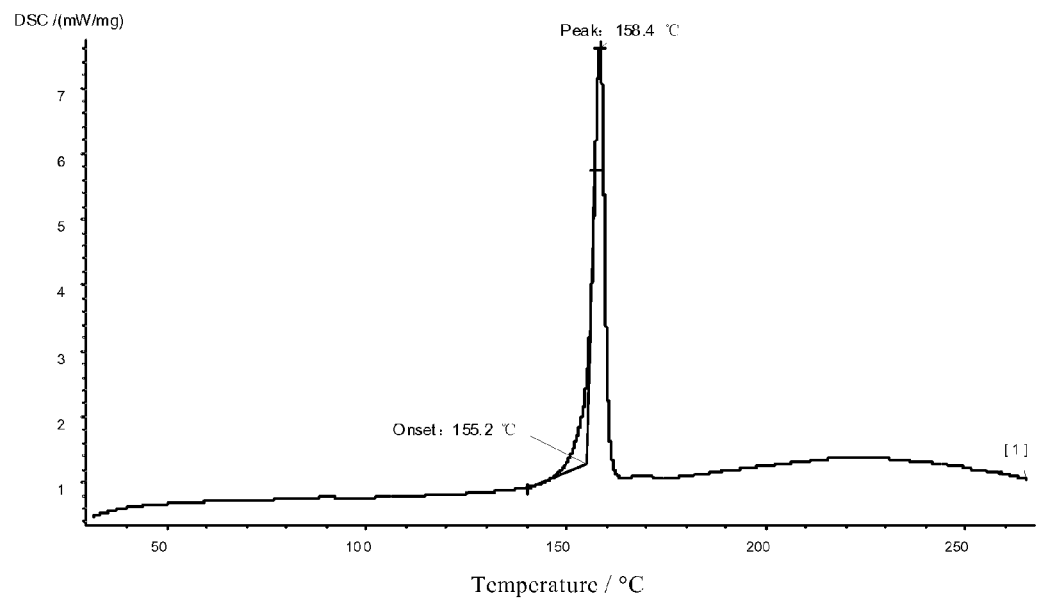
FIG. 2 is the differential scanning calorimetry (DSC) scheme of the crystal Agomelatine sulfuric acid complex.
Figure 3:
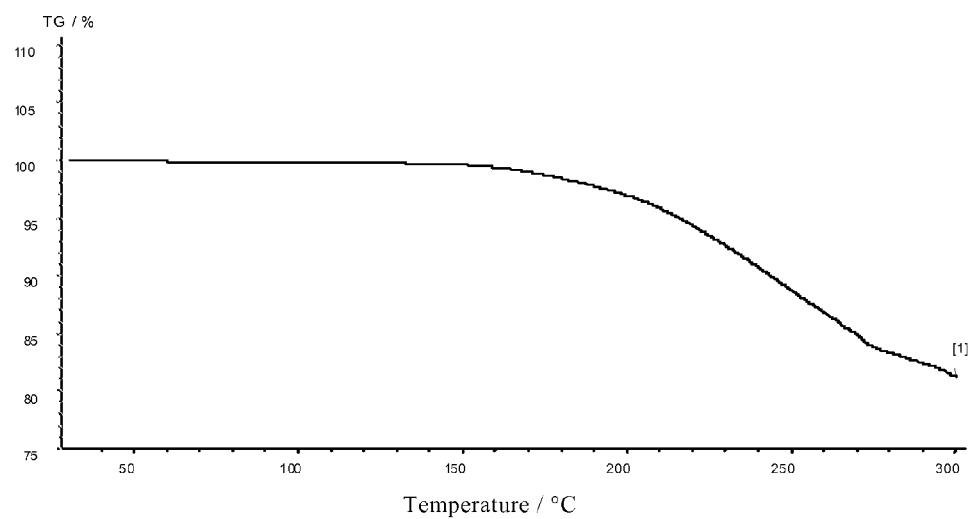
FIG. 3 is the thermogravimetric analysis (TGA) scheme of the crystal Agomelatine sulfuric acid complex.
Figure 4:
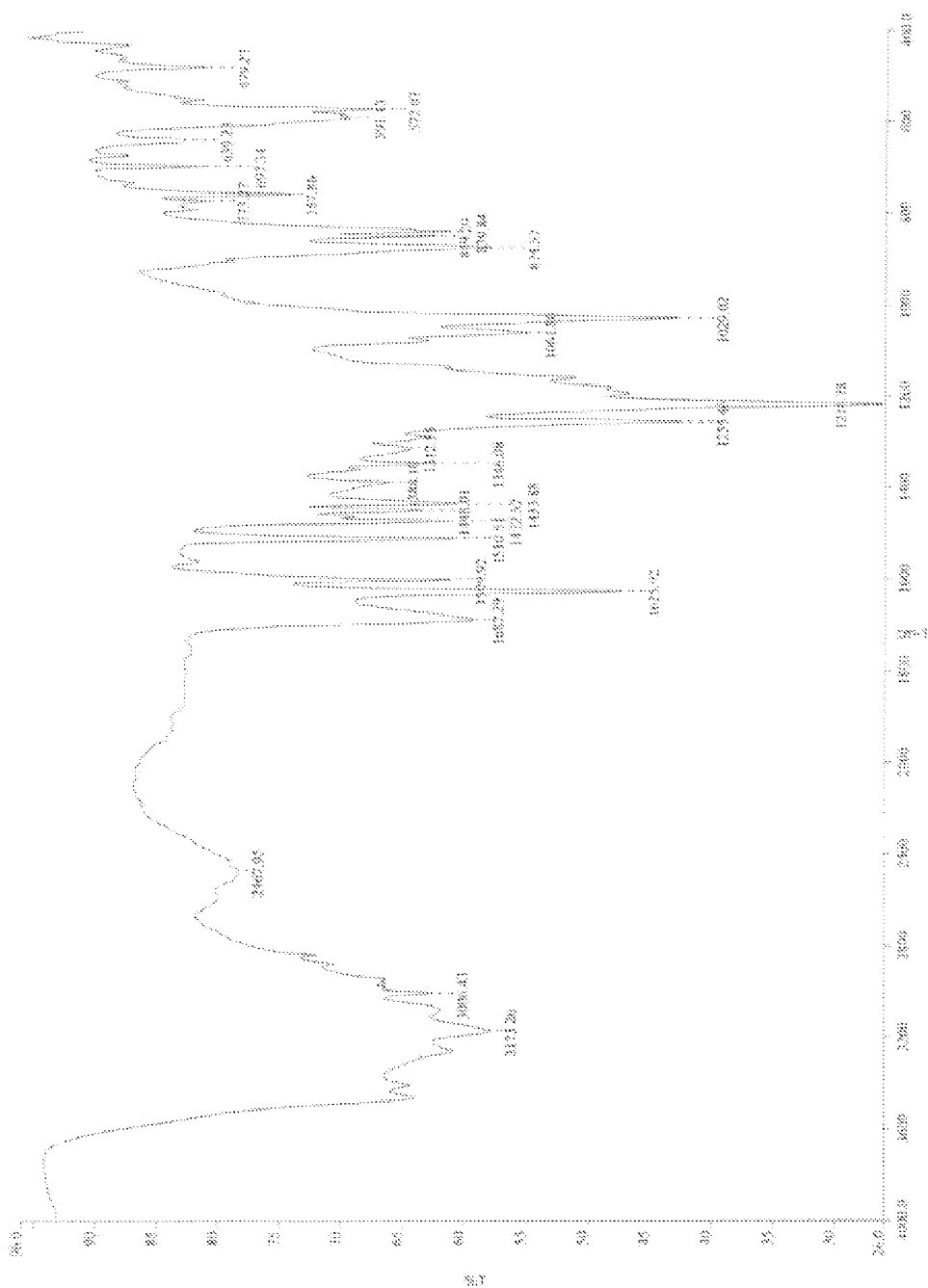
FIG. 4 is the infrared spectrum of the crystal Agomelatine sulfuric acid complex.
Figure 5:
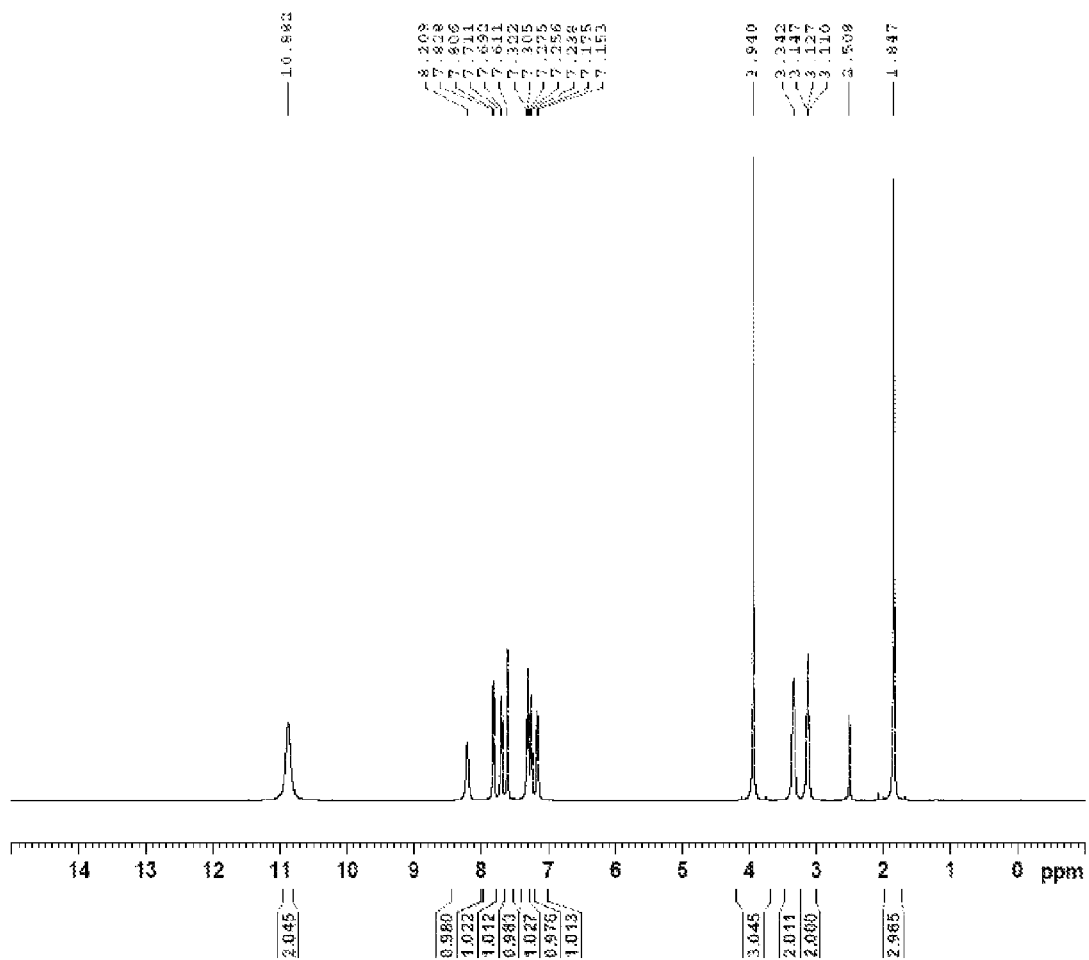
FIG. 5 is the H NMR spectroscopy of the crystal Agomelatine sulfuric acid complex in $d_6$-DMSO.
Figure 6:
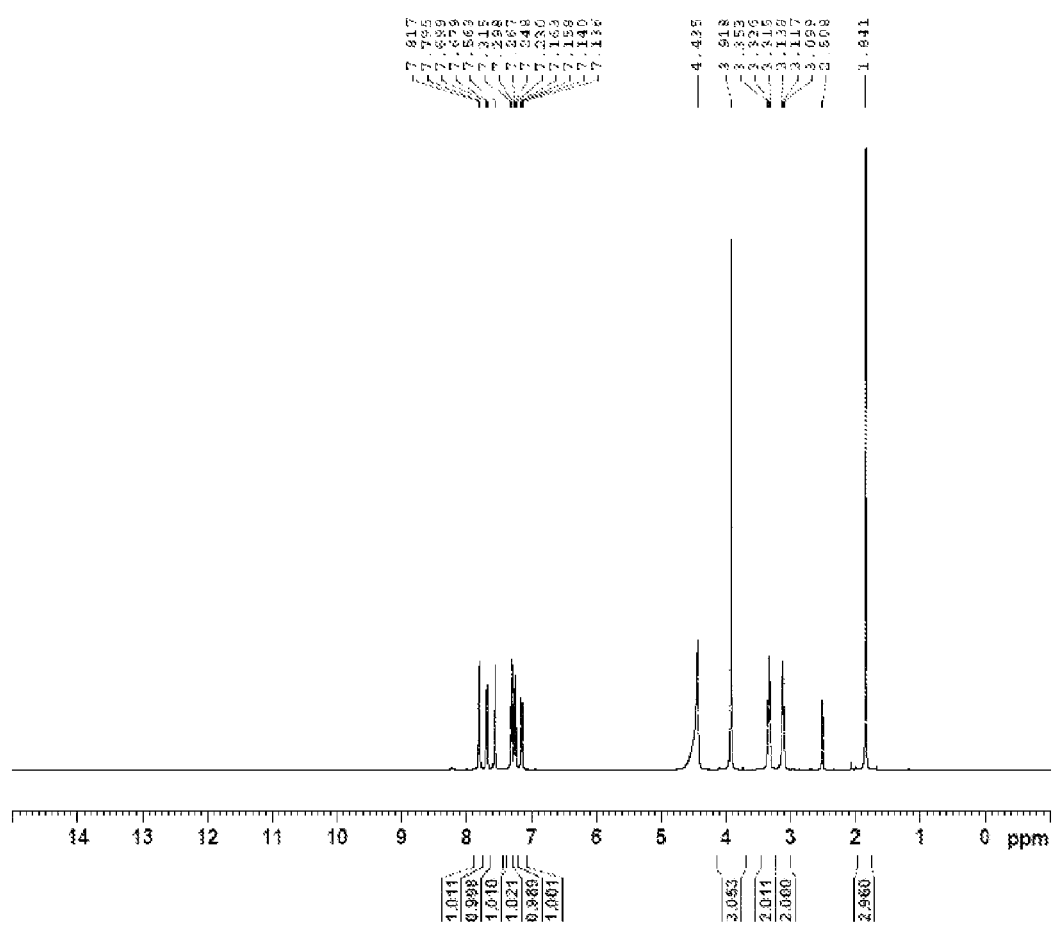
FIG. 6 is the H NMR spectroscopy of the crystal Agomelatine sulfuric acid complex in $d_6$-DMSO+$D_2O$.

10.0 g of Agomelatine was dissolved into 50 mL of acetone under stirring, and 4.2 g of concentrated sulfuric acid (or a pre-formulated concentrated sulfuric acid-acetone solution) was added at 10° C.; stirring under room temperature overnight for complete crystallization; the reaction was filtered, and the crystal was washed with 10 mL of acetone twice, and dried at 80° C. to obtain 13.6 g of product as a white crystal; purity: 99.6%, yield rate: 96.9%. mp: 154.5-158.0° C. $^1$H-NMR (400 MHz, $d_6$-DMSO): δ 10.88 (s, 2H), 8.21 (s, 1H), 7.82 (d, 1H), 7.70 (d, 1H), 7.61 (s, 1H), 7.32-7.24 (m, 2H), 7.16 (d, 1H), 3.94 (s, 3H), 3.34 (b, 2H), 3.12 (t, 2H), 1.85 (s, 3H). $^1$H-NMR (400 MHz, $d_6$-DMSO+$D_2$O): δ 7.80 (d, 1H), 7.69 (d, 1H), 7.56 (s, 1H), 7.32-7.23 (m, 2H), 7.15 (dd, 1H), 3.92 (s, 3H), 3.34 (t, 2H), 3.12 (t, 2H), 1.84 (s, 3H). KF: 0.620%. S element analysis result: ($C_{15}H_{17}NO_2 \cdot H_2SO_4$) calculated value S % (9.39%), actually measured value S % (9.23%). X-powder diffraction spectrum is shown in FIG. 1.

EXAMPLE 3

10.0 g of Agomelatine was dissolved into 20 mL of methanol under stirring, cooled to 0° C. and 4.1 g of sulfuric acid was added; the reaction was stirred and 40 mL of acetone was added; continuous stirring overnight for solid to be completely separated out; the reaction was filtered, and the solid was washed with 10 mL of acetone twice and dried at 80° C. to obtain 12.8 g of product as a white solid; purity: 99.8%, yield rate: 91.2%.

EXAMPLE 4

4.2 g of sulfuric acid was dissolved into 50 mL of acetone under stirring, and 10.0 g of Agomelatine was added at 25° C., allowing the solid to be separated out under stirring, and the stirring was continued overnight for solid to be separated out completely; the reaction was filtered, and the solid was washed with 10 mL of acetone twice and dried at 80° C. to obtain 13.5 g of product as a white solid; purity: 99.3%, yield rate: 96.2%.

EXAMPLE 5

100.0 g of Agomelatine was dissolved into 500 mL of acetone under stirring, and a pre-formulated 41.5 g sulfuric acid/100 mL acetone solution was added below 20° C., maintained below 20° C. under stirring overnight for crystallization; the reaction was filtered, and the crystal was washed with 100 mL acetone twice, and dried at 80° C. to obtain 132.1 g of product as a white crystal; purity: 99.9%, yield rate: 94.1%. mp: 154.5-158.0° C. KF: 0.521%. X-power diffraction result is consistent with that in Example 2.

The Agomelatine content in the product determined by external standard method was 71.48% (theoretic value: 71.27%). The sulfate radical content determined by barium sulfate gravimetric analysis is 28.63% (theoretic value: 28.14%).

EXAMPLE 6

10.00 g of Agomelatine was dissolved into 50 mL of ethyl acetate under stirring, and 3.95 g of methanesulfonic acid was added under 10° C., allowing crystal to be separated out slowly under stirring; the reaction was continuously stirred and cooled to 0° C. for complete crystallization; the reaction was filtered and the crystal was washed with 10 mL of ethyl acetate twice and dried under reduced pressure at 30° C., to obtain 9.14 g of product as a white crystal; purity: 99.7%, yield rate: 65.5%. mp: 75.0-80.0° C. $^1$H-NMR (400 MHz, $CDCl_3$): δ 11.09 (b, 1H), 9.82 (s, 1H), 7.75 (d, 1H), 7.67 (d, 1H), 7.35 (s, 1H), 7.24-7.29 (m, 2H), 7.16 (d, 1H), 3.97 (s, 3H), 3.71 (b, 2H), 3.34 (b, 2H), 2.86 (s, 3H), 2.42 (s, 3H). MS: $ESI^+$ m/z=244.1 $[M+H]^+$, $ESI^-$ m/z=94.93 $[M-H]^+$.

EXAMPLE 7

10.00 g of Agomelatine was dissolved into 50 mL of isopropyl acetate under stirring, and 3.95 g of methanesulfonic acid was added at 10° C.; the reaction was stirred under room temperature (20° C.) overnight for crystallization, and cooled to 0° C. for complete crystallization; the reaction was filtered, and the crystal was washed with 10 mL of isopropyl acetate twice and dried under reduced pressure at 30° C. to obtain 9.95 g of product as a white crystal; purity: 99.7%, yield rate: 71.3%.

EXAMPLE 8

10.00 g of Agomelatine was dissolved into 10 mL of methanol under stirring, then the mixture was cooled to 0° C. and added 3.95 g of methanesulfonic acid; after mixing and dissolving, 70 mL of isopropyl acetate was added and the stirring was continued at 0° C. overnight for complete crystallization; the reaction was filtered, and the crystal was washed with 10 mL of isopropyl acetate twice and dried under reduced pressure at 30° C. to obtain 8.40 g of product as a white crystal; purity: 99.8%, yield rate: 60.2%.

EXAMPLE 9

3.95 g of methanesulfonic acid was dissolved into 50 mL of isopropyl acetate under stirring, and 10.00 g of Agomelatine was added under 20° C.; stirring the mixture for crystallization, then cooling to 0° C. and stirring overnight for complete crystallization; the reaction was filtered, and the crystal was washed twice with 10 mL of isopropyl acetate and dried under reduced pressure at 30° C. to obtain 9.85 g of product as a white crystal; purity: 99.7%, yield rate: 70.6%.

EXAMPLE 10

100.0 g of Agomelatine was dissolved into 500 mL of isopropyl acetate under stirring, and 40.5 g of methanesulfonic acid was added below 20° C.; the temperature was maintained below 20° C. while stirring overnight for crystallization; further cooling to 0° C. and stirring for complete crystallization; the reaction was filtered, and the crystal was washed with 60 mL of isopropyl acetate twice and dried under reduced pressure at 30° C. to obtain 91.6 g of product as a white crystal; purity: 99.7%, yield rate: 65.7%. KF: 0.643%. mp: 75.5-80.0° C.

Figure 7:
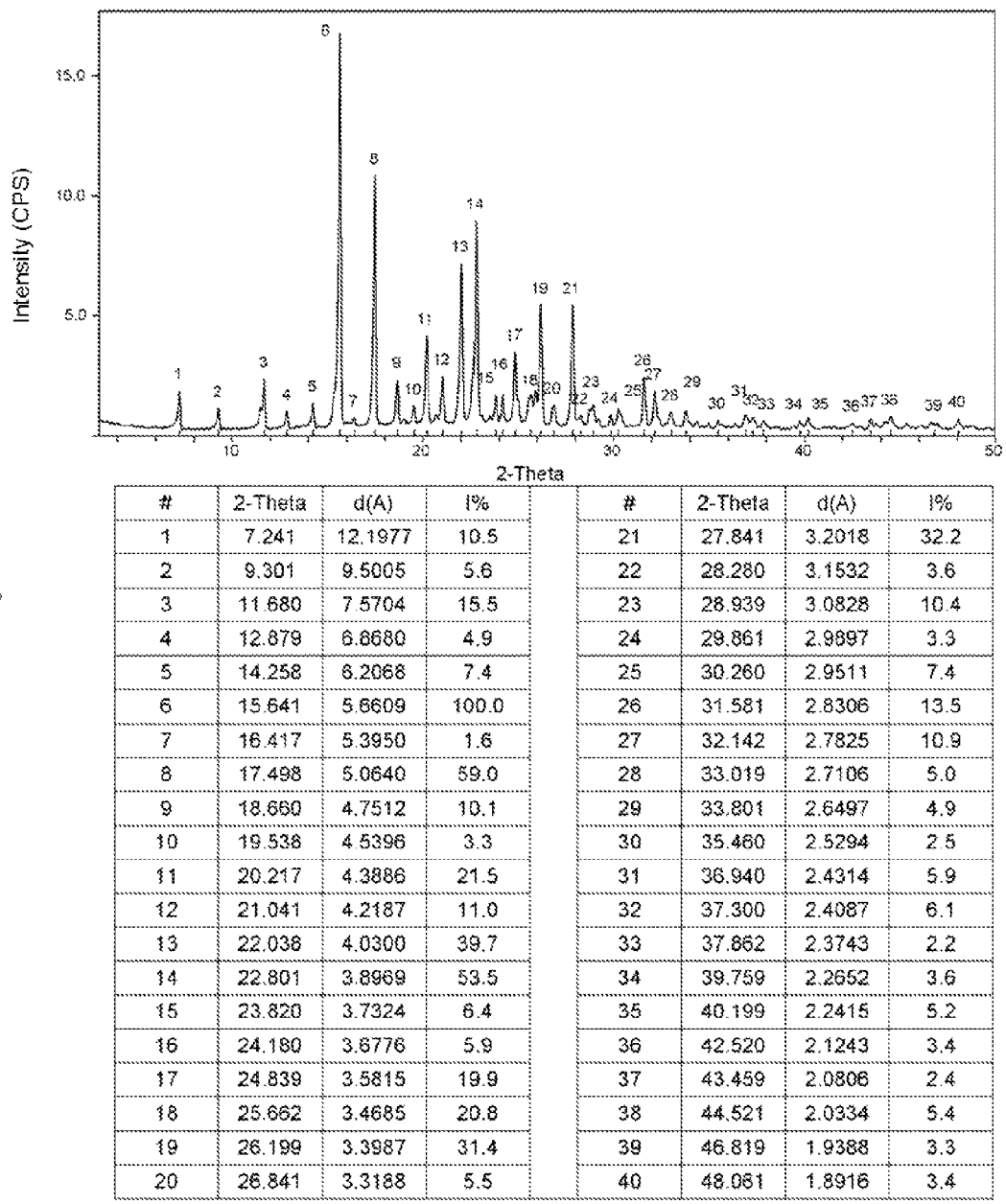
FIG. 7 is the powder X-Ray Diffraction (XRD) spectrum of crystal A of the Agomelatine methanesulfonic acid complex.
Figure 8:
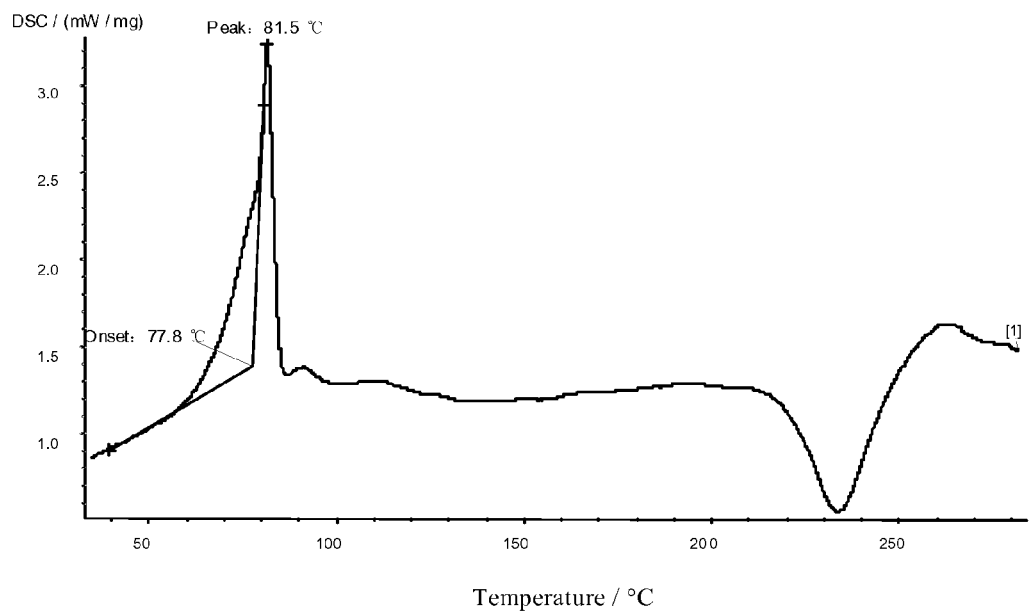
FIG. 8 is the differential scanning calorimetry (DSC) scheme of crystal A of the Agomelatine methanesulfonic acid complex.
Figure 9:
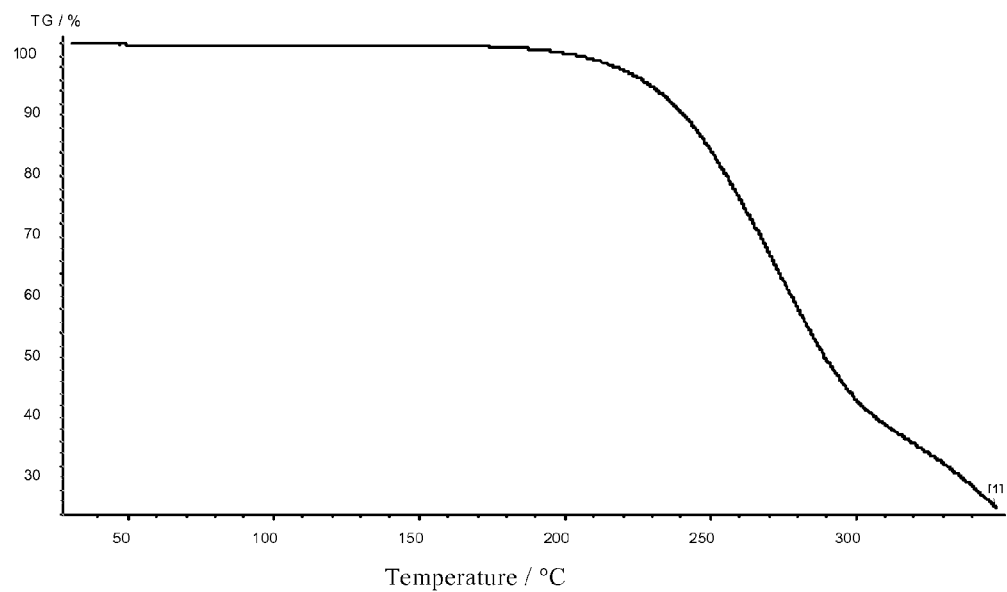
FIG. 9 is the thermogravimetric analysis (TGA) scheme of crystal A of the Agomelatine methanesulfonic acid complex.
Figure 10:
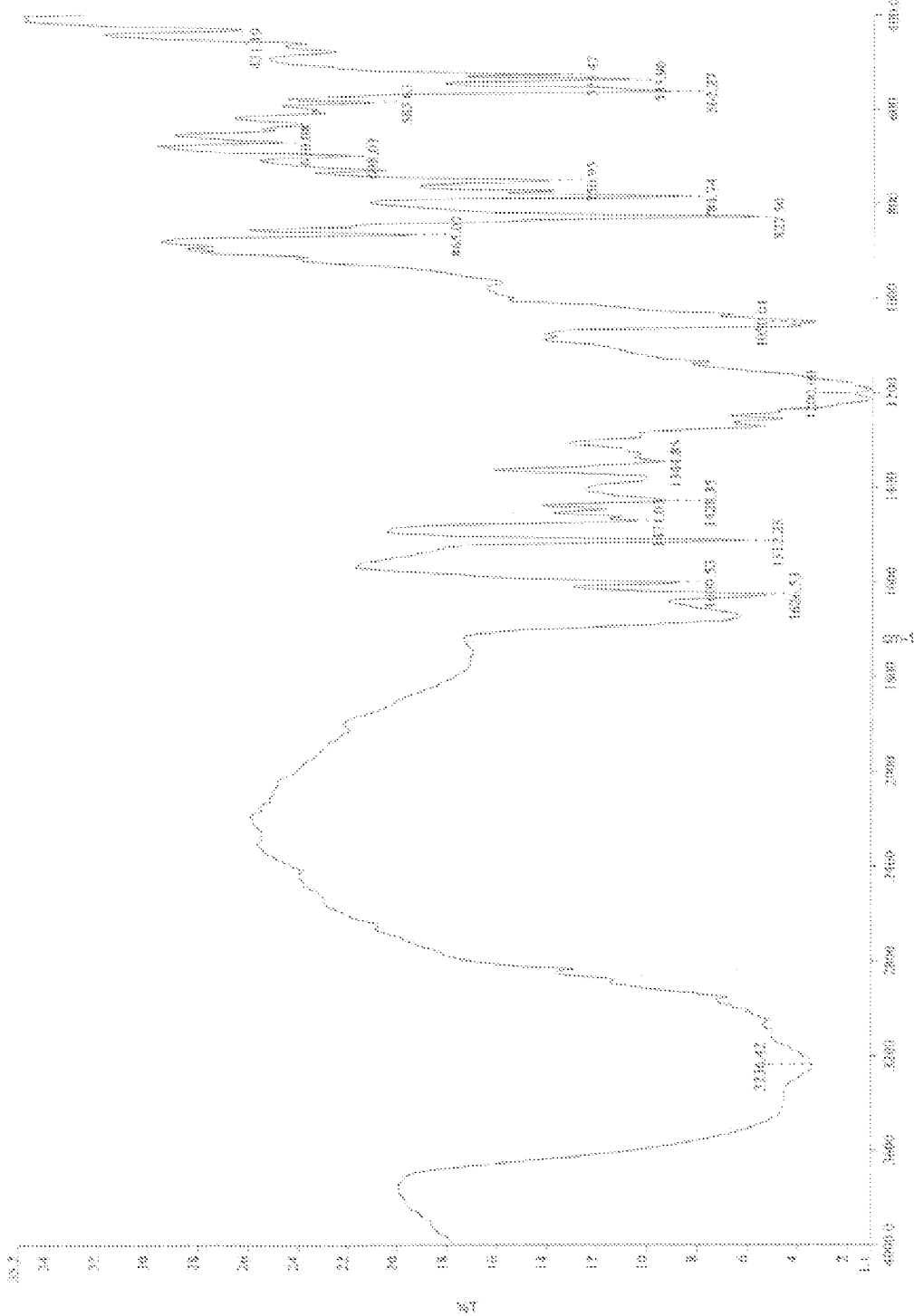
FIG. 10 is the infrared spectrum of crystal A of the Agomelatine methanesulfonic acid complex.

The Agomelatine methanesulfonic acid complexes obtained in Example 6-10 above are determined as crystallographic form A via X-power diffraction, and the typical X-powder diffraction spectrum is shown in FIG. 7.

EXAMPLE 11

Figure 11:
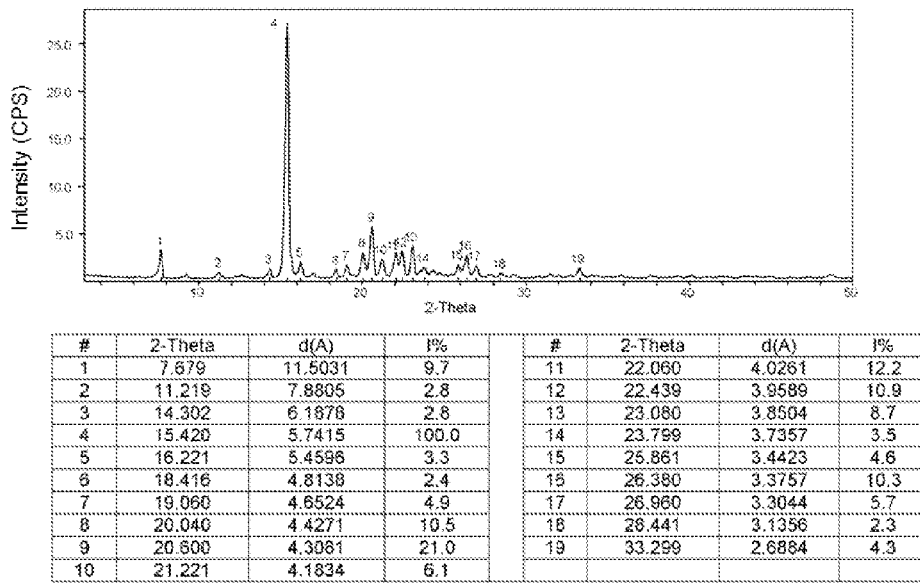
FIG. 11 is the powder X-Ray Diffraction (XRD) spectrum of crystal B of the Agomelatine methanesulfonic acid complex.
Figure 12:
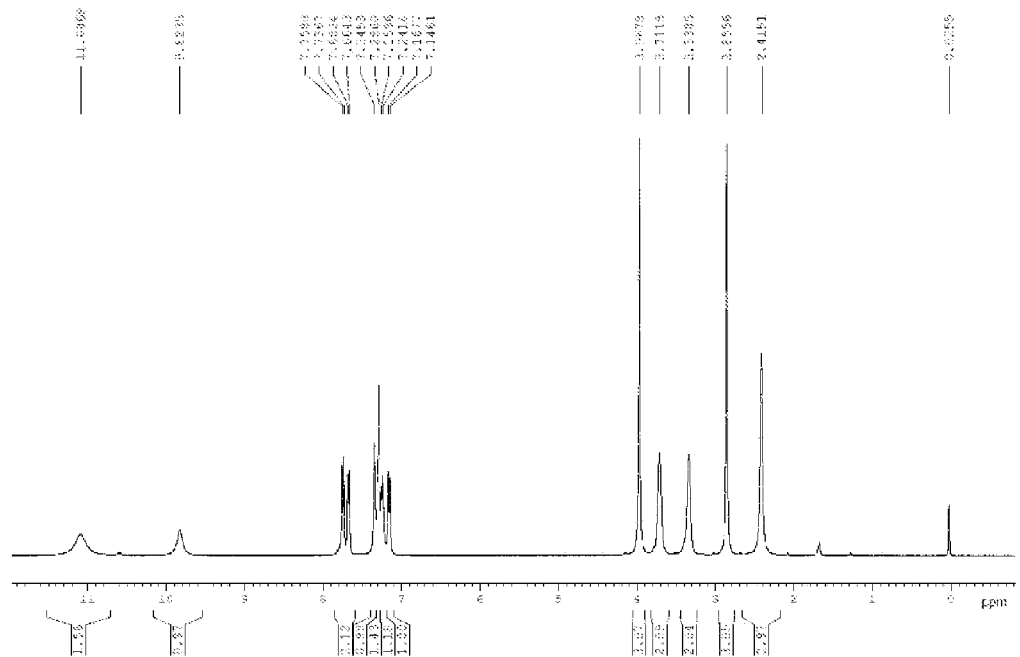
FIG. 12 is the H NMR spectroscopy of the crystal Agomelatine methanesulfonic acid complex in $CDCl_3$.
Figure 13:
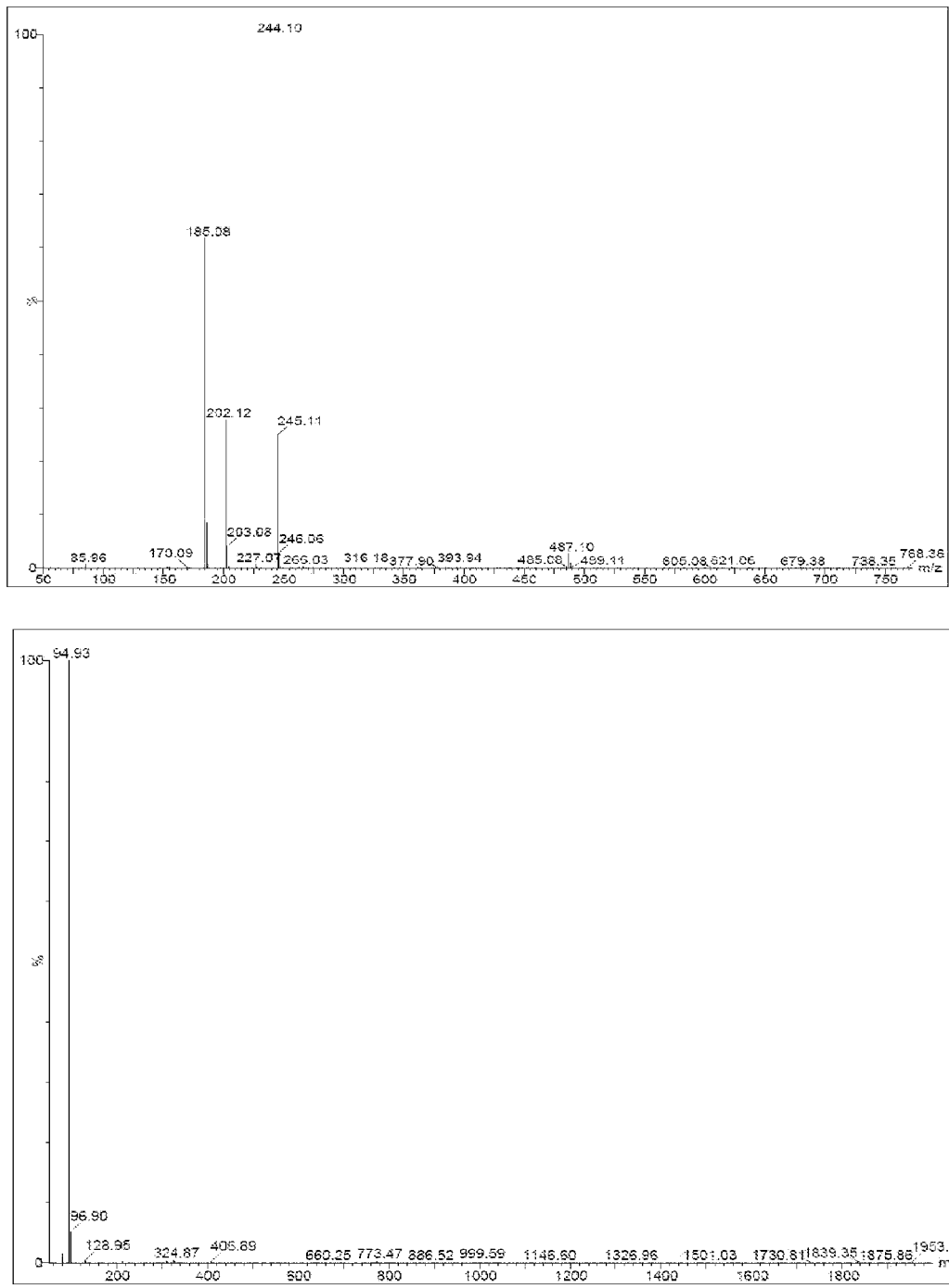
FIG. 13 is the MS data of the crystal Agomelatine methanesulfonic acid complex.

10.0 g of Agomelatine methanesulfonic acid complex was heated and dissolved into a mixed solvent containing 10 mL of methanol and 50 mL of ethyl acetate or excess ethyl acetate, and cooled to −10° C., and maintained at this temperature for 12 hours or longer, then Agomelatine methanesulfonic acid complex crystal was allowed to be separated out slowly, which was filtered and dried, and determined as crystallographic form B via X-powder diffraction (see FIG. 11). yield rate: 63%.

EXAMPLE 12

Figure 14:
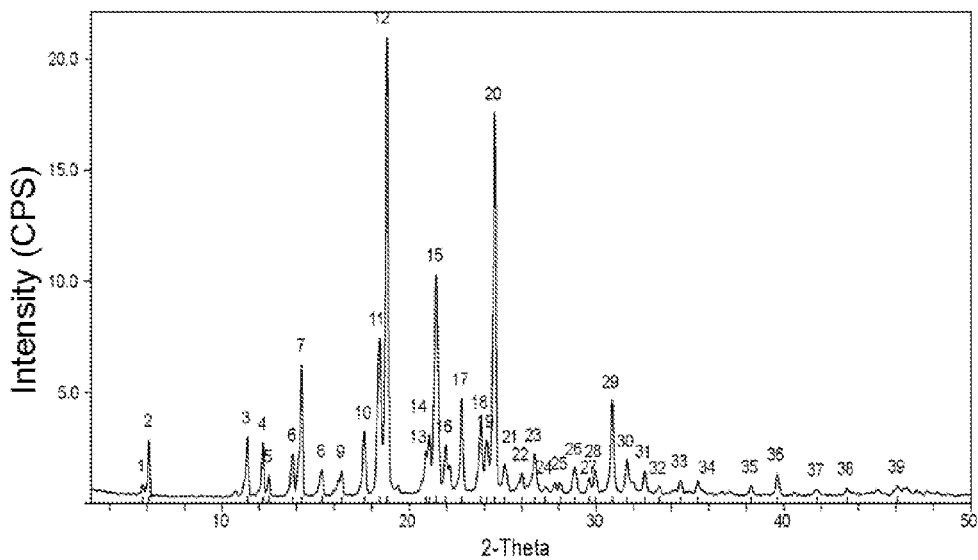
FIG. 14 is the powder X-diffraction scheme of the crystal Agomelatine benzenesulfonic acid complex.

10.0 g of Agomelatine was dissolved into 50 mL of dichloromethane under stirring, added with 6.5 g of benzenesulfonic acid under atmospheric temperature, slow crystallization was allowed during stirring; the reaction was continuously stirred and cooled to 10° C. for complete crystallization; the reaction was filtered and the crystal was washed with 10 mL of dichloromethane twice, and dried at 80° C. to obtain 15.6 g of product as a white crystal; purity: 99.5%, yield rate: 94.5%. mp: 131.0-136.0° C. $^1$H-NMR (400 MHz, CD$_3$OD) δ 7.84~7.87 (m, 2H), 7.78 (d, 1H), 7.69 (d, 1H), 7.49 (d, 1H), 7.44~7.47 (m, 3H), 7.33 (d, 1H), 7.27 (t, 1H), 7.15 (dd, 1H), 3.98 (s, 3H), 3.60 (t, 2H), 3.28 (t, 2H), 2.09 (s, 3H). X-powder diffraction please see FIG. 14.

EXAMPLE 13

Figure 15:
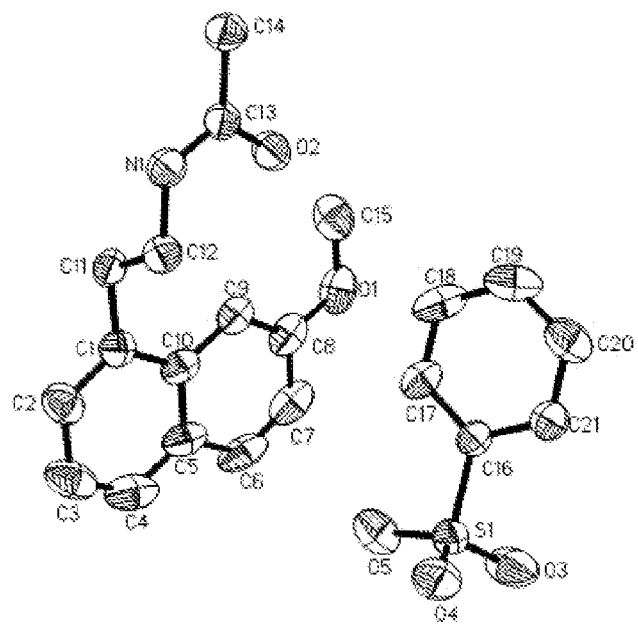
FIG. 15 is the single crystal stereochemical structure projection of the crystal Agomelatine benzenesulfonic acid complex.
Figure 16:
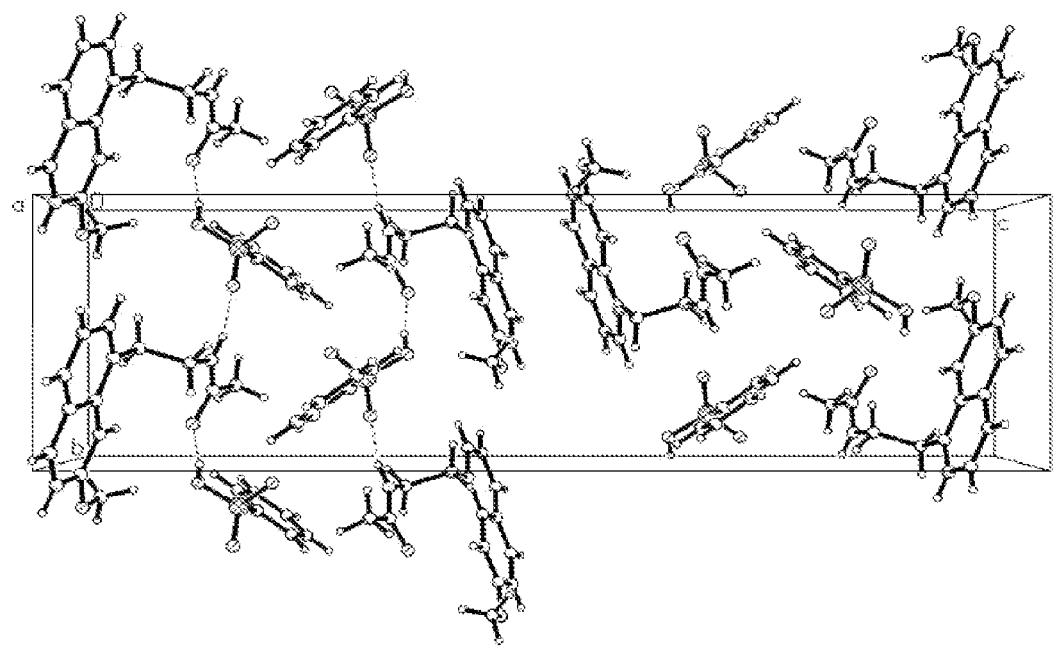
FIG. 16 is the cell accumulation projection of the crystal Agomelatine benzenesulfonic acid complex.
Figure 17:
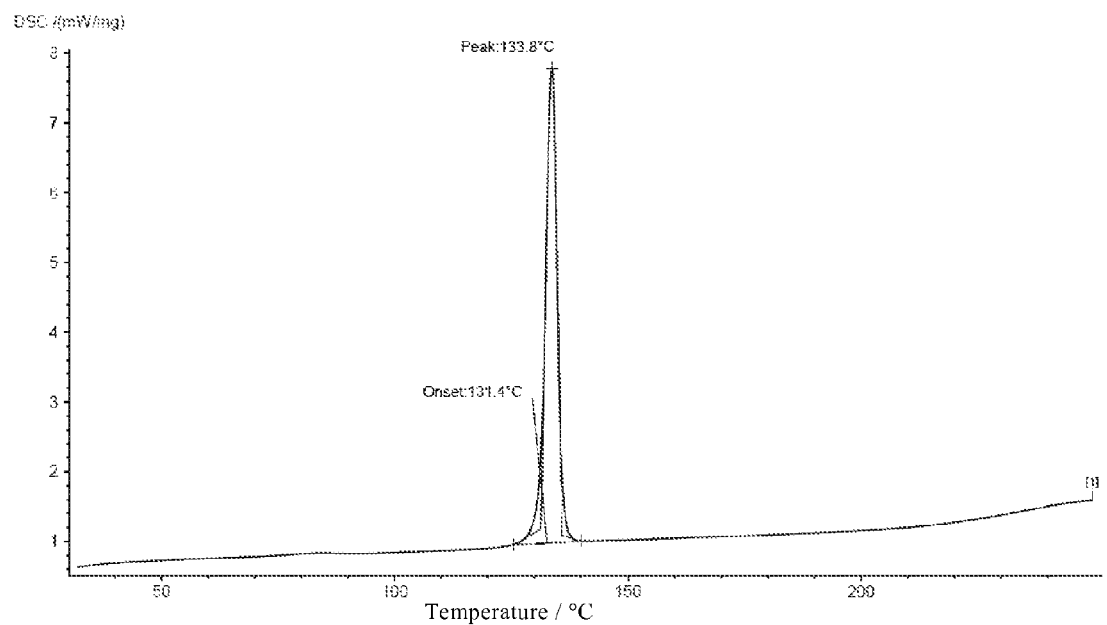
FIG. 17 is the differential scanning calorimetry (DSC) scheme of the crystal Agomelatine benzenesulfonic acid complex.
Figure 18:
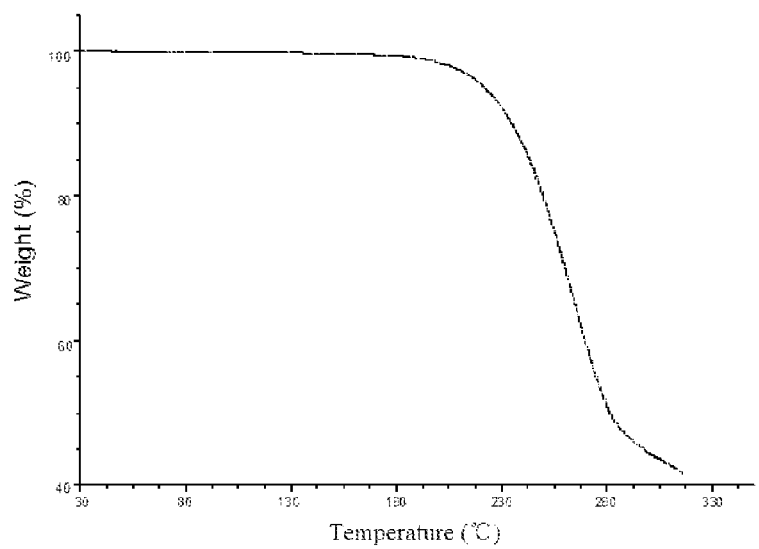
FIG. 18 is the thermogravimetric analysis (TGA) scheme of the crystal Agomelatine benzenesulfonic acid complex.
Figure 19:
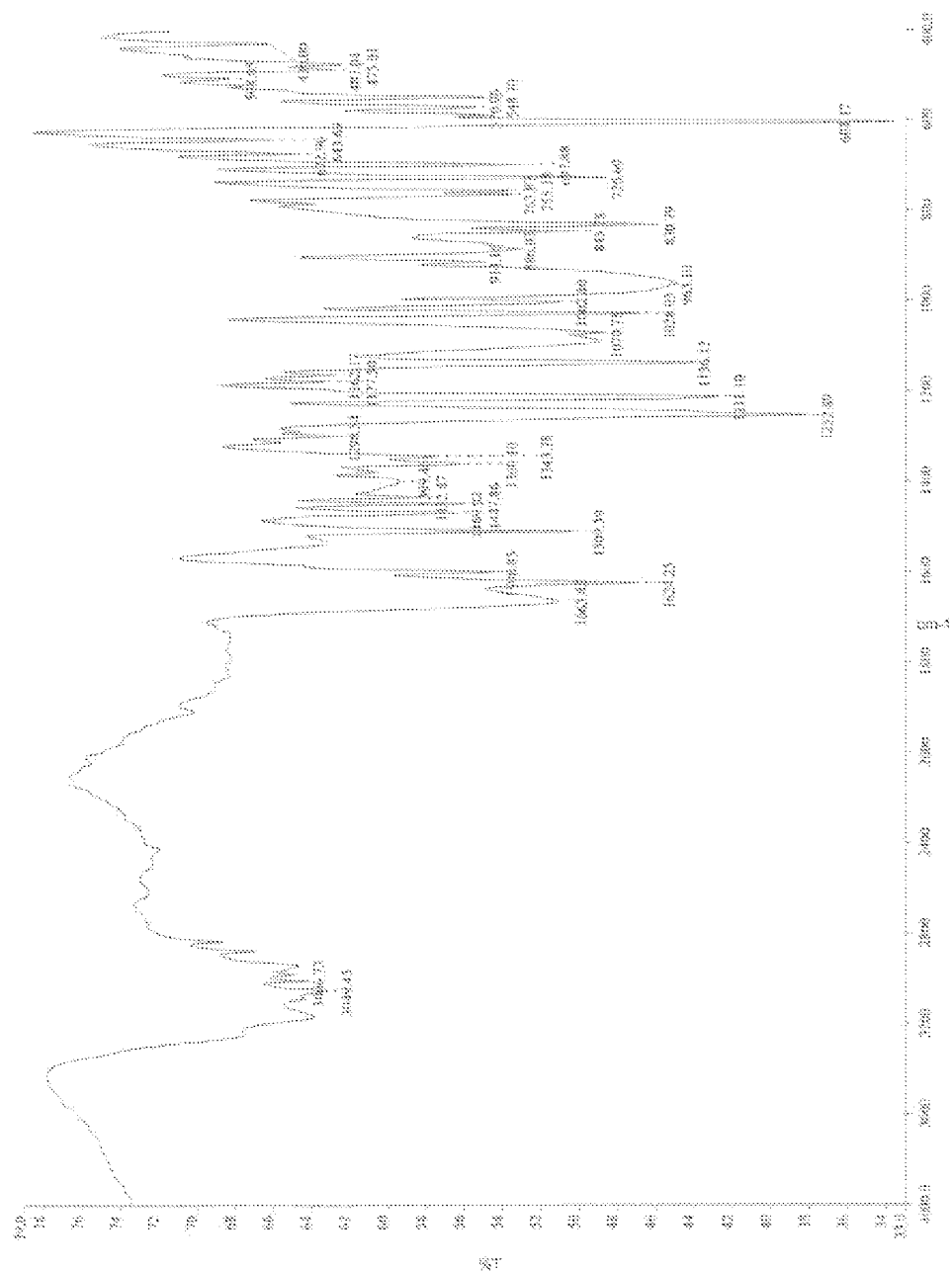
FIG. 19 is the infrared spectrum of the crystal Agomelatine benzenesulfonic acid complex.
Figure 20:
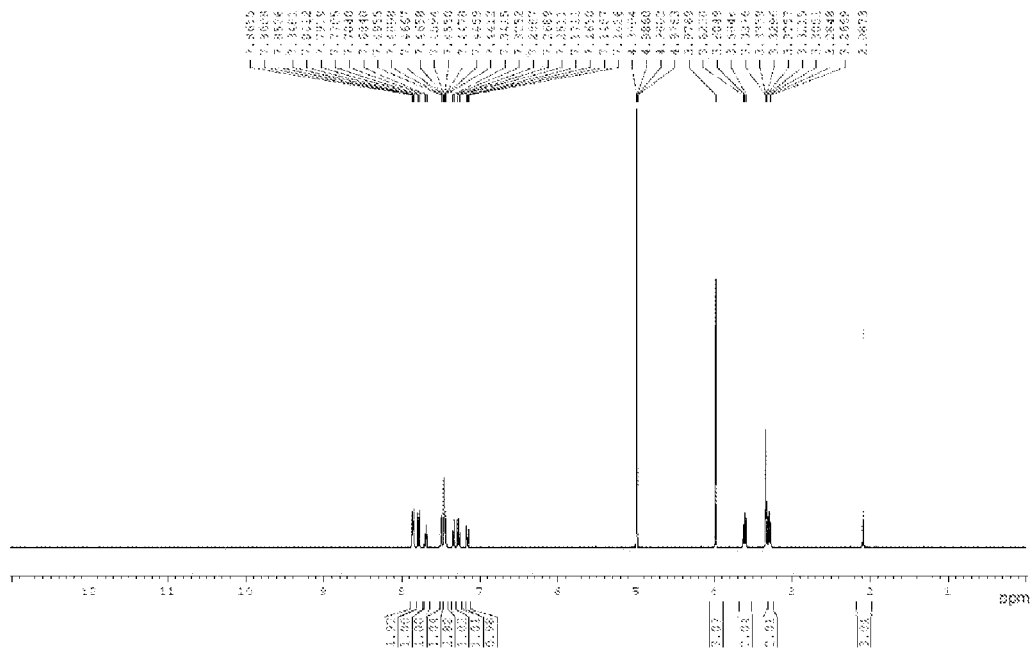
FIG. 20 is the H NMR spectrum of the crystal Agomelatine benzenesulfonic acid complex.
Figure 21:
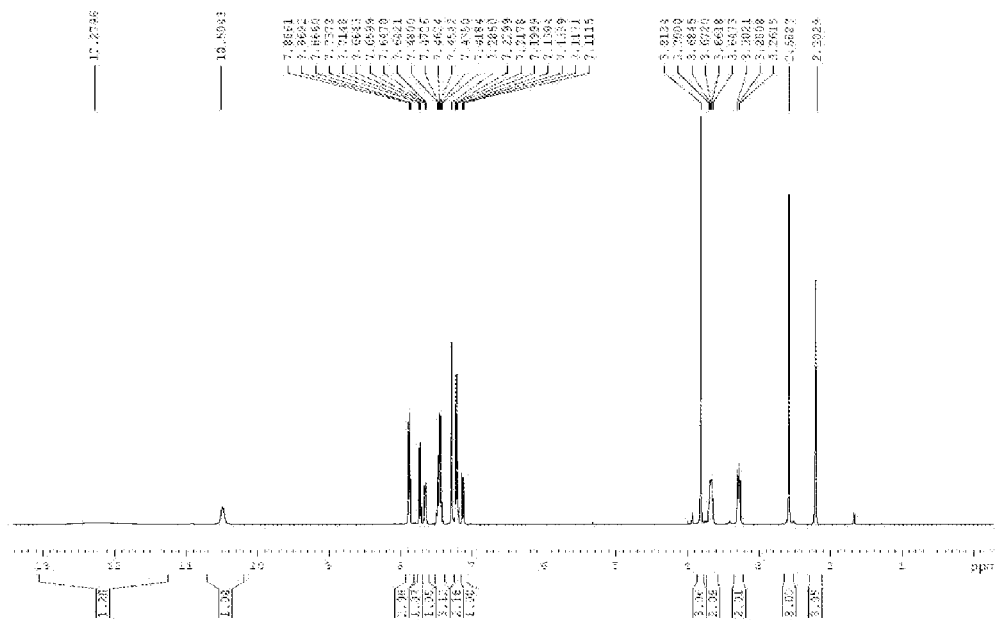
FIG. 21 is the H NMR spectrum of the Agomelatine benzenesulfonic acid complex.

10.0 g of Agomelatine was dissolved into 50 mL of acetone under stirring, added with 6.5 g of benzenesulfonic acid at 10° C., and the reaction was stirred overnight for complete crystallization; the reaction was filtered and the crystal was washed with 10 mL of acetone twice, and dried at 80° C. to obtain 15.4 g of product as a white crystal; purity: 99.6%, yield rate: 93.3%. mp: 133.0-135.0° C. Optionally, the experiment above was repeated, wherein the stirring was stopped after achieving a homogeneous reaction, which was allowed to stand still overnight and the crystal was separated out the next day; single crystal was picked out for structure determination via X-diffraction. Results are shown in FIGS. 15 and 16.

EXAMPLE 14

10.0 g of Agomelatine was dissolved into 20 mL of methanol under stirring, and the reaction was cooled to 0° C. before adding 6.5 g of benzenesulfonic acid, and stirred for dissolution; 40 mL of acetone was added and the reaction was continuously stirred overnight for complete crystallization; the reaction was filtered and the crystal was washed with 10 mL of acetone twice, and dried at 80° C. to obtain 15.0 g of product as a white crystal; purity: 99.8%, yield rate: 90.9%. mp: 133.0-135.0° C.

EXAMPLE 15

6.5 g of benzenesulfonic acid was dissolved into 50 mL of acetone under stirring, and added with 10.0 g of Agomelatine under 25° C., the solid was allowed to be separated out while stirring; the reaction was continuously stirred overnight for complete crystallization; the reaction was filtered and the crystal was washed with 10 mL of acetone twice, and dried at 80° C. to obtain 15.8 g of product as a white crystal; purity: 99.3%, yield rate: 95.8%. mp: 131.0-136.0° C.

EXAMPLE 16

100.0 g of Agomelatine was dissolved into 600 mL of acetone under stirring, and added with 65.0 g of benzenesulfonic acid at a temperature below atmospheric temperature; the reaction was stirred below atmospheric temperature for crystallization; the reaction was filtered and the solid was washed with 100 mL of acetone twice, dried at 80° C. to obtain 150.1 g of product as a white crystal; purity: 99.9%, yield rate: 91.0%. mp: 133.0-134.5° C.

The crystals obtained in Examples 13-16 have the X-powder diffraction results consistent with that in Example 12.

EXAMPLE 17

1.0 g of Agomelatine was dissolved into 5 mL of acetone under stirring, and 0.7 g p-toluenesulfonic acid was added at 10° C.; the reaction was stirred at 0-5° C. overnight for solid to be completely separated out; the reaction was filtered and the solid was washed with 2 mL of acetone twice, and dried at 60° C. twice to obtain 1.5 g of product as a off-white solid; purity: 99.0%, yield rate: 88.2%. $^1$H-NMR (400 MHz, CDCl$_3$) δ 12.28 (br-s, 1H), 10.50 (s, 1H), 7.87~7.89 (m, 2H), 7.72 (d, 1H), 7.64~7.66 (dd, 1H), 7.42~27.48 (m, 3H), 7.20~7.23 (m, 2H), 7.11~7.14 (dd, 1H), 3.81 (s, 3H), 3.65~3.70 (m, 2H), 3.26~3.30 (m, 2H), 2.58 (s, 3H), 2.20 (s, 3H).

EXAMPLES 18-25

| Example | HX type | Reference Method | Reaction Solvent | Poor Solvent | Yield rate |
|---|---|---|---|---|---|
| 18 | H$_2$SO$_4$ | Example 3 | dichloromethane | ethyl acetate | 92.6% |
| 19 | H$_2$SO$_4$ | Example 3 | dichloromethane | acetone | 92.0% |
| 20 | RSO$_3$H (R = CH$_3$) | Example 8 | tetrahydrofuran | ethyl acetate | 59.5% |
| 21 | RSO$_3$H (R = CH$_3$) | Example 8 | acetone | isopropyl acetate | 63.2% |
| 22 | RSO$_3$H (R = Ph) | Example 14 | acetonitrile | ethyl acetate | 87.3% |
| 23 | RSO$_3$H (R = Ph) | Example 14 | chloroform | acetone | 91.4% |

-continued

| Example | HX type | Reference Method | Reaction Solvent | Poor Solvent | Yield rate |
|---|---|---|---|---|---|
| 24 | $RSO_3H$ (R = Ph) | Example 14 | dichloromethane | methyl isobutyl ketone | 91.9% |
| 25 | $RSO_3H$ (R = $CH_3Ph$) | Example 14 | methanol | ethyl acetate | 73.2% |

The Agomelatine used in the above Examples is commercially available, or can be prepared according to method in the art.

EXAMPLE 26

Pharmaceutical Composition of the Agomelatine Sulfuric Acid Complex 1,000 capsules were made with the sulfuric acid complex, the methanesulfonic acid complex or the benzenesulfonic acid complex prepared in Examples 5, 10 or 16 as the crude drug, each containing 25 mg of Agomelatine. Similarly, 1,000 capsules as a reference group were made with the commercially available Agomelatine (AG) crystallographic form II.

| HX acid radical type | HX = $H_2SO_4$ Example 5 | HX = $CH_3SO_3H$ Example 10 | HX = $PhSO_3H$ Example 16 | AG reference group (crystallographic form II) |
|---|---|---|---|---|
| Agomelatine sulfuric acid complex | 35.1 g | 34.9 g | 41.3 g | 25.0 g |
| lactose Tablettose ® 100 | 80.4 g | 80.6 g | 78.6 g | 82.6 g |
| starch (1500) | 26.5 g | 26.5 g | 24.5 g | 28.5 g |
| sodium carboxymethyl starch | 8.7 g | 8.8 g | 8.5 g | 9.2 g |
| croscarmellose sodium | 17.6 g | 17.6 g | 15.8 g | 18.4 g |
| stearic acid | 3.5 g | 3.5 g | 3.0 g | 3.8 g |

Described above are only the preferred Examples of the present invention, and those skilled in the art can understand that various improvements and optimizations can be made under the principle of the present invention, and these improvements and optimizations should also be considered as falling into the protection scope of the present invention.

Detection Methods and Results:

1. Determination of Purity

Conditions for chromatogram: octadecyl silane chemically bonded silica was used as a filler; a mixed solution wherein methanol-acetonitrile-phosphate buffer (10 mM/L, pH adjusted to 2.7 with phosphoric acid)=40:20:40 was used as mobile phase; column temperature was 40° C.; detecting wavelength was 220 nm. The purity of each of the products in the above described Example was determined using internal standard method.

1 mg/mL of solution for each test was formulated with the mobile phase, wherein 10 μL was taken and injected into the liquid phase chromatograph. Chromatogram map was recorded and the purity results were shown in the above Examples.

2. Determination of Stability

Three batches of each of the Agomelatine sulfuric acid complex provided according to the present invention were tested under an accelerated testing condition, i.e., stored in a constant hymidity cabinet under a temperature of (40±2°) C., and a relative humidity of (75±5)% for 6 months. The stability of each of the batches was studied via High Performance Liquid Chromatography (HPLC) and the content percentage of the total related substances (total impurities) was determined in addition to the peaks of Agomelatine and acid radicals. The results are listed as follow:

| Acid radical complex | Time (month) | 0 | 1 | 2 | 3 | 6 |
|---|---|---|---|---|---|---|
| Agomelatine sulfuric acid complex (total impurities %) | Batch 1 | 0.11 | 0.12 | 0.12 | 0.13 | 0.13 |
| | Batch 2 | 0.12 | 0.12 | 0.13 | 0.13 | 0.14 |
| | Batch 3 | 0.14 | 0.14 | 0.15 | 0.15 | 0.16 |
| Agomelatine methanesulfonic acid complex (Total impurities %) | Batch 1 | 0.21 | 0.22 | 0.22 | 0.23 | 0.23 |
| | Batch 2 | 0.22 | 0.22 | 0.23 | 0.23 | 0.24 |
| | Batch 3 | 0.24 | 0.24 | 0.25 | 0.25 | 0.26 |
| Agomelatine benzenesulfonic acid complex (Total impurities %) | Batch 1 | 0.11 | 0.12 | 0.12 | 0.14 | 0.14 |
| | Batch 2 | 0.12 | 0.12 | 0.14 | 0.14 | 0.15 |
| | Batch 3 | 0.14 | 0.14 | 0.16 | 0.16 | 0.17 |

It can be seen from the table above that under the accelerated testing condition, the content of the total related substances (total impurities) within the Agomelatine sulfuric acid complex prepared according to the present invention did not vary significantly as a function of time, suggesting that the Agomelatine sulfuric acid complex prepared according to the present invention can be provided with good stability, which is favorable for drug safety.

3. Determination of Test Contents Via External Standard Method.

Solution Formulation:

Reference solution: 5.0 mg of Agomelatine standard was precisely weighed and placed into a 25 ml volumetric flask, dissolved with mobile phase, and diluted to the scale.

Test solution: 6.8 mg of the product from Example 5 (Agomelatine sulfuric acid complex) was precisely weighed and placed into a 25 ml volumetric flask, dissolved with mobile phase, and diluted to the scale.

Each of the reference solution and test solution was taken and injected into the chromatograph, and the chromatographic map was recorded.

Calculation:

$$W = \frac{A_T}{A_R} \times \frac{C_R}{C_T} \times 100\%$$

wherein W is the Agomelatine content in the test;

$A_T$, and $A_R$ are the peak areas of the Agomelatine within the test solution and reference solution, respectively;

$C_T$ is the concentration of the Agomelatine within the test solution, mg/ml $C_R$ is the concentration of the Agomelatine within the reference solution, mg/ml 4. Determination of Water Solubility:

The solubility of the Agomelatine sulfuric acid complex test, the Agomelatine methanesulfonic acid complex test, or the Agomelatine sulfuric acid complex test, for example according to Example 5, 10 or 16, in pure water, 0.1 mol/L hydrochloric acid aqueous solution or a buffer solution (pH=7.0) was determined using external standard method, and the solubility of the commercially available Agomelatine crystallographic form II in the solutions described above was determined for comparison, with the results listed in the following table.

| Test | Agomelatine content (mg/ml) | | |
|---|---|---|---|
| | pury water | 0.1 mol/L hydrochloric acid aqueous solution | pH = 7.0 buffer solution |
| Agomelatine crystallographic form II | 0.27 | 0.29 | 0.26 |
| Agomelatine sulfuric acid complex | 0.34 | 0.40 | 0.33 |
| Agomelatine methanesulfonic acid complex | 0.36 | 0.39 | 0.32 |
| Agomelatine benzenesulfonic acid complex | 0.30 | 0.38 | 0.29 |

It can be seen from the comparison data in the above table that the solubility of the Agomelatine sulfuric acid complex prepared according to the present invention in pure water, 0.1 mol/L hydrochloric acid aqueous solution close to human gastric juice environment, or the buffer solution (pH=7.0) is better than solubility of Agomelatine, suggesting that the acid radical complexes of the present invention are provided with a better bioavailability.

5. Representative Experiments of Dissolution Rate:

The dissolution rate of the capsule group in Example 26 was detected with 0.1 mol/L hydrochloric acid as the dissolution medium. The results are listed in the following table: each of the Agomelatine sulfuric acid complex groups is represented as HX=$H_2SO_4$ group, HX=$CH_3SO_3H$ group or HX=$PhSO_3H$ group.

| Capsule Group | Point in Time Dissolution Rate (%) | | | | | |
|---|---|---|---|---|---|---|
| | 5 minutes | 10 minutes | 15 minutes | 30 minutes | 45 minutes | 60 minutes |
| AG reference group | 61 | 85 | 90 | 92 | 92 | 94 |
| HX = $H_2SO_4$ group | 82 | 93 | 95 | 96 | 95 | 98 |
| HX = $CH_3SO_3H$ group | 85 | 95 | 95 | 94 | 96 | 98 |
| HX = $PhSO_3H$ group | 78 | 85 | 91 | 93 | 95 | 95 |

It can be seen obviously from the dissolution rate data in the table that compared with the available Agomelatine crystallographic form II capsules, the Agomelatine sulfuric acid complex capsule groups of the present invention present higher dissolution rates in the 0.1 mol/L hydrochloric acid aqueous solution close to human gastric juice environment, and achieve the peak value faster. Therefore, it is expected that the capsule groups of the present invention have the advantage of rapid complete dissolution in human body.

6. Structural Analysis of Crystal:

6.1 Diffraction Experiment:

Crystal was prepared with the single crystal obtained in Example 2. The crystal used for the diffraction experiment was colorless and transparent columnar, with a crystal size of 0.13×0.16×0.25 mm, belonging to orthorhombic crystal system, space group $P2_12_12_1$, cell parameters: a=8.0780(5)Å, b=8.5765(6)Å, c=28.920(2)Å, α=β=γ=90.0°, cell volume V=2003.6(2)Å$^3$, and the number of asymmetric units in the cell Z=4.

Diffraction intensity data was collected with Bruker SMART APEX-II diffractometer, under the condition: $CuK_\alpha$ radiation, graphite monochromator, single vessel diameter φ=0.50 mm, distance between the crystal and CCD detector d=60.3 mm, vessel pressure 40 kV, vessel flow 30 mA, scanning mode: Φ/ω scanning, total diffraction point number collected: 9647, independent diffraction point number: 3395, observable point number ($|F|^2 \geq 2\sigma|F|^2$): 3221.

6.2 Single Crystal Structural Analysis:

Crystal structures were analyzed using a direct method (Shelxs97), and the positions of all of the 28 non-hydrogen atoms were obtained. The structural parameters were corrected with the least square method and the types of the atoms were distinguished. The positions of all of the hydrogen atoms were obtained using geometry calculation method and differential Fourier method, the final reliable factor $R_1$=0.0480, $wR_2$=0.1379(w=1/σ|F|$^2$), S=1.067. The stoichiometric formula of one asymmetric unit was finally determined as $C_{15}H_{17}NO_2 \cdot C_6H_6O_3S$, with a calculated crystal density of 1.331 g/cm$^3$.

Molecular stereochemical structure projection please see FIG. 15, and the cell accumulation projection please see FIG. 16.

7. Crystallographic Form Analysis:
7.1 X-Powder Diffraction Analysis:
Instrument model: BRUKER-AXS D8 ADVANCE Powder X-Ray Diffractometer
Testing condition: Cu targer Ka 1; working voltage: 40 kv/40 mA; step length: 0.02; scanning rate: 0.2 sec/step.
7.2 Differential Scanning Calorimety (DSC):
Instrument model: PerkinElmer Thermal Analysis System-7 Differential Scanning calorimeter;
Testing condition: heating rate: 10° C./min, temperature range: 30-280° C.
7.3 Thermogravimetic Analysis (TGA):
Instrument model: PerkinElmer Thermal Analysis;
Testing condition: heating rate: 10° C./min, temperature range: 25-350° C.

The invention claimed is:

1. An Agomelatine acid complex as in formula I:

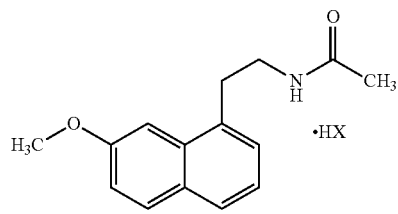

wherein HX is $H_2SO_4$ or $CH_3SO_3H$, and wherein the Agomelatine acid complex is a crystalline solid.

2. The Agomelatine acid complex according to claim 1, wherein the crystallographic form of the crystalline solid is determined using X-powder diffraction technology with the Bragg 2-Theta, interplanar spacing (d) and relative intensity (I) characterized as follows:

| HX = $H_2SO_4$ (Agomelatine sulfuric acid complex) | | |
|---|---|---|
| 2-Theta | d(Å) | Relative Intensity (I %) |
| 6.959 | 12.6922 | 13.7 |
| 11.621 | 7.6087 | 64.8 |
| 14.139 | 6.2587 | 18.1 |
| 16.979 | 5.2177 | 22.3 |
| 17.640 | 5.0236 | 56.7 |
| 18.660 | 4.7512 | 90.6 |
| 19.818 | 4.4762 | 17.1 |
| 20.541 | 4.3202 | 56.6 |
| 21.659 | 4.0996 | 19.9 |
| 23.420 | 3.7953 | 76.5 |
| 23.961 | 3.7107 | 22.9 |
| 24.461 | 3.6361 | 88.0 |
| 24.841 | 3.5813 | 100.0 |
| 25.799 | 3.4505 | 15.8 |
| 27.040 | 3.2949 | 19.7 |
| 27.881 | 3.1973 | 26.3 |
| 30.220 | 2.9550 | 17.9 |
| 30.781 | 2.9024 | 16.9 |

| HX = $CH_3SO_3H$ (Agomelatine methanesulfonic acid complex) crystallographic form A | | |
|---|---|---|
| 2-Theta | d(Å) | Relative Intensity (I %) |
| 7.241 | 12.1977 | 10.5 |
| 9.301 | 9.5005 | 5.6 |
| 11.680 | 7.5704 | 15.5 |

-continued

| HX = $CH_3SO_3H$ (Agomelatine methanesulfonic acid complex) crystallographic form A | | |
|---|---|---|
| 2-Theta | d(Å) | Relative Intensity (I %) |
| 12.879 | 6.8680 | 4.9 |
| 14.258 | 6.2068 | 7.4 |
| 15.641 | 5.6609 | 100.0 |
| 17.498 | 5.0640 | 59.0 |
| 18.660 | 4.7512 | 10.1 |
| 20.217 | 4.3886 | 21.5 |
| 21.041 | 4.2187 | 11.0 |
| 22.038 | 4.0300 | 39.7 |
| 22.801 | 3.8969 | 53.5 |
| 24.839 | 3.5815 | 19.9 |
| 26.199 | 3.3987 | 31.4 |
| 26.841 | 3.3188 | 5.5 |
| 27.841 | 3.2018 | 32.2 |
| 31.581 | 2.8306 | 13.5 |
| 32.142 | 2.7825 | 10.9 | or

| HX = $CH_3SO_3H$ (Agomelatine methanesulfonic acid complex) crystallographic form B | | |
|---|---|---|
| 2-Theta | d(Å) | Relative Intensity (I %) |
| 7.679 | 11.5031 | 9.7 |
| 14.302 | 6.1878 | 2.8 |
| 15.420 | 5.7415 | 100.0 |
| 16.221 | 5.4596 | 3.3 |
| 18.416 | 4.8138 | 2.4 |
| 19.060 | 4.6524 | 4.9 |
| 20.040 | 4.4271 | 10.5 |
| 20.600 | 4.3081 | 21.0 |
| 21.221 | 4.1834 | 6.1 |
| 22.060 | 4.0261 | 12.2 |
| 22.439 | 3.9589 | 10.9 |
| 23.080 | 3.8504 | 8.7 |
| 25.861 | 3.4423 | 4.6 |
| 26.380 | 3.3757 | 10.3 |
| 26.960 | 3.3044 | 5.7 |
| 33.299 | 2.6884 | 4.3 | wherein crystals of the crystalline solid in which the diffraction peaks are within the error limits of ±0.2° are also included.

3. A method for preparing the Agomelatine acid complex according to claim 1, comprising forming a complex by reaction between the Agomelatine and the corresponding acid HX.

4. The method for preparing the Agomelatine acid complex according to claim 1, comprising forming a complex by reaction between the Agomelatine and the corresponding acid HX in an organic solvent.

5. The method for preparing the Agomelatine acid complex according to claim 3, comprising dissolving Agomelatine into an organic solvent before adding a corresponding acid, and separating the crystal or precipitate out during the reaction as a product.

6. The method for preparing the Agomelatine acid complex according to claim 3, comprising dissolving Agomelatine into an organic solvent before adding a corresponding acid, and then adding another poor solvent; separating the crystal or precipitate out during the reaction as a product.

7. The method for preparing the Agomelatine acid complex according to claim 3, comprising adding Agomelatine into an organic solvent containing the corresponding acid, separating the crystal or precipitate out during the reaction as a product.

8. The method for preparing the Agomelatine acid complex according to claim 4, further comprising washing and drying the crystal or precipitate separated out.

9. The method for preparing the Agomelatine acid complex according to claim 4, wherein the temperature of the reaction is 35° C. or lower.

10. The method for preparing the Agomelatine acid complex according to claim 4, wherein the organic solvent is selected from the group consisting of: dichloromethane, chloroform, acetone, methyl isobutyl ketone, C1-C4 alcohol, methyl acetate, ethyl acetate, isopropyl acetate, tetrahydrofuran, methyltetrahydrofuran, acetonitrile and any combination thereof.

11. method for preparing the Agomelatine acid complex according to claim 10, wherein when HX is $H_2SO_4$, the organic solvent is dichloromethane, acetone, or a combination thereof; and when HX is $CH_3SO_3H$, the organic solvent is dichloromethane, acetone, C1-C4 alcohol or combination thereof.

12. The method for preparing the Agomelatine acid complex according to claim 6, wherein the poor solvent is selected from the group consisting of methyl acetate, ethyl acetate, isopropyl acetate, acetone, methyl isobutyl ketone and any combination thereof.

13. The method for preparing the Agomelatine acid complex according to claim 12, wherein when HX is $H_2SO_4$, the poor solvent is ethyl acetate, isopropyl acetate or acetone; and when HX is $CH_3SO_3H$, the poor solvent is ethyl acetate, isopropyl acetate or acetonean.

14. The method for preparing the Agomelatine methanesulfonic acid complex crystallographic form B according to claim 2, comprising heating and dissolving the Agomelatine methanesulfonic acid complex into a mixed solvent containing methanol and ethyl acetate, or into excess ethyl acetate, cooling slowly to −10° C., and maintaining at this temperature for 12 hours or longer, allowing the Agomelatine methanesulfonic acid complex crystallographic form B to be separated out slowly.

15. A pharmaceutical composition consisting of an effective amount of the Agomelatine acid complex according to claim 1 and one or more of a pharmaceutically acceptable excipient.

16. A method of treating melatoninergic system diseases, sleep disturbance, nervousness, anxiety, seasonal affective disorder, cardiovascular diseases, digestive system diseases, fatigue, schizophrenia, panic disorder, and/or depression comprising administering to a patient in need of such treatment, a therapeutically effective amount of the Agomelatine acid complex according to claim 1.

17. The method for preparing the Agomelatine acid complex according to claim 9, wherein the temperature of the reaction is 0°–20° C.

* * * * *